United States Patent
Chassot et al.

(10) Patent No.: US 6,780,998 B2
(45) Date of Patent: *Aug. 24, 2004

(54) SUBSTITUTED 2-AMINOALKYL-1,4-DIAMINOBENZENE COMPOUNDS AND OXIDATION DYE PRECURSOR COMPOSITIONS CONTAINING SAME

(75) Inventors: Laurent Chassot, Praroman (CH); Hans-Juergen Braun, Ueberstorf (CH)

(73) Assignee: Wella Aktiengesellschaft, Darmstadt (DE)

(*) Notice: Subject to any disclaimer, the term of this patent is extended or adjusted under 35 U.S.C. 154(b) by 80 days.

This patent is subject to a terminal disclaimer.

(21) Appl. No.: 10/124,149

(22) Filed: Apr. 17, 2002

(65) Prior Publication Data

US 2002/0189033 A1 Dec. 19, 2002

Related U.S. Application Data

(62) Division of application No. 10/251,765, filed on Sep. 20, 2002, now Pat. No. 6,685,751, which is a division of application No. 09/692,971, filed on Oct. 20, 2000, now Pat. No. 6,436,152.

(30) Foreign Application Priority Data

Dec. 18, 1999 (DE) .......................... 199 61 272

(51) Int. Cl.$^7$ .................. C07D 213/74; C07D 207/04; C07C 229/00; A61K 7/13
(52) U.S. Cl. .................. 546/304; 546/216; 546/329; 546/300; 546/149; 544/162; 544/402; 548/335.5; 548/537; 548/543; 548/550; 548/532; 548/566; 549/80; 549/439; 549/440; 549/492; 562/442; 562/443; 564/306; 564/305; 564/336; 564/372; 8/409; 8/405; 8/406; 8/407; 8/408

(58) Field of Search .................. 546/216, 329, 546/300, 304, 149; 544/162, 402; 548/335.5, 537, 543, 550, 532, 566; 549/80, 439, 440, 492; 562/442, 443; 564/306, 305, 336, 372

(56) References Cited

U.S. PATENT DOCUMENTS

3,743,509 A * 7/1973 Baltazzi .................. 430/186
6,602,302 B1 * 8/2003 Chassot et al. .................. 8/405
2002/0144357 A1 * 10/2002 Lim et al. .................. 8/405

* cited by examiner

*Primary Examiner*—Evelyn Mei Huang
(74) *Attorney, Agent, or Firm*—Michael J. Striker

(57) ABSTRACT

The oxidation hair dye precursor composition contains from 0.005 to 20.0 percent by weight of one or more coupler compounds and from 0.005 to 20.0 percent by weight of one or more developer compounds. The one or more developer compounds include at least one substituted 2-aminoalkyl-1,4-diaminobenzene compound of the formula (I):

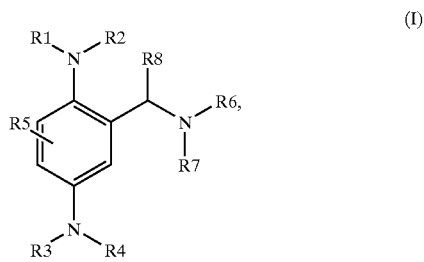

(I)

New substituted 2-aminoalkyl-1,4-diaminobenzene compounds of formula (I) are described.

5 Claims, No Drawings

SUBSTITUTED 2-AMINOALKYL-1,4-DIAMINOBENZENE COMPOUNDS AND OXIDATION DYE PRECURSOR COMPOSITIONS CONTAINING SAME

CROSS-REFERENCE

This is a divisional of U.S. Patent Application, Ser. No. 10/251,765, filed on Sep. 20, 2002, now U.S. Pat. No. 6,685,751, This is a divisional of Ser. No. 09/692,971 filed Oct. 20, 2000, now U.S. Pat. No. 6,436,152.

BACKGROUND OF THE INVENTION

1. Field of the Invention

The present invention relates to compositions for dyeing keratin fibers based on a developer-coupler substance combination, which contain at least one substituted 2-aminoalkyl-1,4-diaminobenzene compound as the developer substance. It also relates to new substituted 2-aminoalkyl-1,4-diaminobenzene compounds.

2. Prior Art

Oxidation dye precursor compounds have been important in the field of dyeing keratin fibers, especially hair, for a long time. The dye compounds for dyeing the keratin fibers are produced by reaction of certain developer substances with certain coupler substances in the presence of a suitable oxidizing agent. The following compounds are examples of developer substances: 2,5-diaminotoluene, 2,5-diaminophenylethyl alcohol, p-aminophenol and 1,4-diaminobenzene. The following compounds are examples of coupler substances: resorcinol, 4-chlororesorcinol, 1-naphthol, 3-aminophenol and derivatives of m-phenylenediamines.

There are numerous additional requirements of oxidation dye precursor compounds for dyeing human hair besides the resulting color in the desired intensity. The dye precursor compounds must be unobjectionable in toxicological and dermatological respects and the resulting hair color of the dyed hair must have good light fastness, permanent wave fastness, acid fastness and rubbing fastness. The color produced by dyeing the hair with the oxidation dye precursor compounds must remain stable in the presence of light, rubbing and chemical agents for at least four to six weeks. Moreover a broad palette of various color shades can be produced by combination of suitable developer and coupler substances.

The requirements for oxidation dye precursor compounds however cannot be completely fulfilled in every way with the currently known dye precursor compounds, as has been stated in the Monograph by K. H. Schrader, "Foundations and Formulations of Cosmetics [Grundlagen und Rezepturen der Kosmetika]", 2nd Edition, pp. 784–799 (1989). There is therefore a need for new developer substances, which fulfill the above-described requirements to a special extent.

SUMMARY OF THE INVENTION

It is therefore an object of the present invention to provide improved developer compounds for use in a method of dyeing keratin fibers, especially human hair.

It is also an object of the present invention to provide new substituted 2-aminoalkyl-1,4-diaminobenzene compounds for use as developer substances in oxidation dye precursor compositions.

It has now been found surprisingly that certain substituted 2-aminoalkyl-1,4-diaminobenzene compounds of the general formula (I) fulfill the special requirements for developer substances to an especially great extent. When these developer substances are used together with most known coupler substances especially intense colors are produced, which are extraordinarily light-fast and wash-fast.

The new substituted 2-aminoalkyl-1,4-diaminobenzene compounds of the formula (I) according to the invention are:

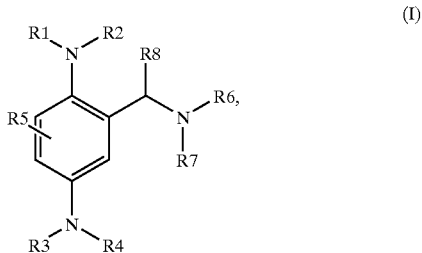

(I)

wherein R1, R2, R3 and R4, independently of each other, are each hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_2$)alkyl group, or R1 and R2 or R3 and R4 together with the nitrogen atom form a four member to eight member aliphatic ring, and wherein at least two of the R1, R2, R3 and R4 substituent groups represent hydrogen;

R5 represents hydrogen, a halogen atom, a $C_1$- to $C_4$-alkyl group, a $C_1$- to $C_4$-hydroxyalkyl group or a $C_1$- to $C_4$-alkoxy group;

R6 and R7, independently of each other, each represent hydrogen, a $C_1$- to $C_2$-alkoxy group, a $C_1$- to $C_6$-alkyl group, a $C_1$- to $C_6$-alkenyl group, a $C_1$- to $C_4$-hydroxyalkyl group, a $C_3$- to $C_4$-dihydroxyalkyl group, a $C_1$- to $C_4$-aminoalkyl group, a $C_1$- to $C_4$-dimethylaminoalkyl group, a $C_1$- to $C_4$-acetylaminoalkyl group, a $C_1$- to $C_4$-methoxyalkyl group, a $C_1$- to $C_4$-ethoxyalkyl group, a $C_1$- to $C_4$-cyanoalkyl group, a $C_1$- to $C_4$-carboxyalkyl group, a $C_1$- to $C_4$-aminocarbonylalkyl group, a pyridylmethyl group, a furfuryl group, a hydrogenated furfuryl group, a substituted pyridyl group, a group of the formula II:

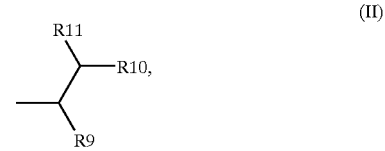

(II)

a group of the formula III:

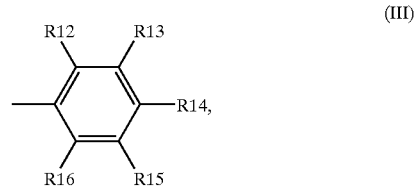

(III)

a group of the formula IV:

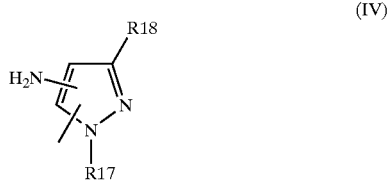

wherein at least one of the R6 and R7 groups is not hydrogen, or R6 and R7 together with the nitrogen atom form one of the following rings:

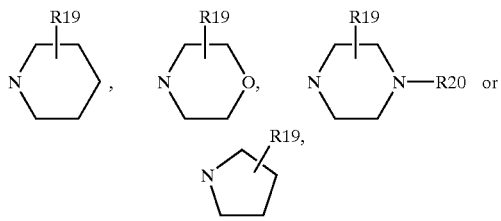

R8 represents hydrogen or a $C_1$- to $C_6$-alkyl group;

R9 represents hydrogen, a carboxy group or an aminocarbonyl-group;

R10 and R11, independently of each other, each represent hydrogen, a hydroxy group, an aminocarbonyl group, a methylthiomethyl group, a substituted phenyl group having a phenyl group substituent or a hydroxy group substitutent or a group of the formula:

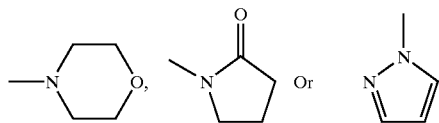

R12, R13, R14, R15 and R16 are each, independently of each other, hydrogen, a halogen atom, a cyano group, a hydroxy group, a $C_1$- to $C_4$-alkoxy group, a $C_1$- to $C_4$-hydroxyalkoxy group, a $C_1$- to $C_6$-alkyl group, a $C_1$- to $C_4$-alkylthioether group, a mercapto group, a nitro group, an amino group, an alkylamino group, a hydroxyalkylamino group, a dialkylamino group, a di(hydroxyalkyl)amino group, a (dihydroxyalkyl) amino group, a (hydroxyalkyl)alkylamino group, a trifluoromethane group, a —C(O)H group, a —C(O) $CH_3$ group, a —C(O)$CF_3$ group, a —Si$(CH_3)_3$ group, a $C_1$- to $C_4$-hydroxyalkyl group, a $C_3$- to $C_4$-dihydoxyalkyl group, or two of the groups R12 to R16 next to each other form an —O—$CH_2$—O— bridge;

R17 represents a $C_1$- to $C_4$-alkyl group or a a $C_1$- to $C_4$-hydroxyalkyl group;

R18 represents hydrogen or a $C_1$- to $C_6$-alkyl group;

R19 represents one or more hydrogen, or hydroxy-, carboxy-, aminocarbonyl-, or hydroxymethyl group; and R20 represents hydrogen or a $C_1$- to $C_6$-alkyl group, with the proviso that R1, R2 and R8 are not each hydrogen when (i) R3 and R4 are a $C_1$- to $C_4$-alkyl group or R3 and R4 together with the nitrogen atom form a morpholino-, pyrrolidino-, piperidino- or hexamethyl-enimino ring, and when (ii) R5 is in the 5-position of the aromatic ring and R5 is hydrogen, a $C_1$- to $C_4$-alkyl group or a halogen atom, and when (iii) R6 and R7, independently of each other, are a $C_1$- to $C_4$-alkyl group or a phenyl group or R3 and R4 taken together with the nitrogen atom form an unsubstituted piperidino- or pyrrolidino-ring;

or a physiologically compatible, water-soluble salt thereof.

The following are examples of the compounds of formula (I): 2-(2,3-dihydroxypropyl)aminomethyl -1,4-diaminobenzene; 2-ethylaminomethyl -1,4-diaminobenzene; 2-(isopropylaminomethyl)-1,4-diaminobenzene; 2-propylaminomethyl -1,4-diaminobenzene; 2-pyrrolidin-1-yl-methyl-1,4-diaminobenzene; 2-[(2-methoxyethylamino)methyl]-1,4-diaminobenzene; 2-morpholin-4-yl-methyl -1,4-diaminobenzene; 2-(2,5-diaminobenzylamino)-butan-1-ol; 2-{[(furan-2-ylmethyl)amino]methyl)-1,4-diaminobenzene; N-(2,5-diaminobenzyl)-O,N-dimethylhydroxylamine; 2-(4-methylpiperazin-1-yl-methyl)-1,4-diaminobenzene; 1-(2,5-diaminobenzyl)piperidin-4-ol; N-[2-(2,5-diaminobenzylamino)ethyl]acetamide; 2-[(2-morpholin-4-yl-ethylamino)methyl]-1,4-diaminobenzene; 2-allylaminomethyl-1,4-diaminobenzene; 2-(2,5-diaminobenzylamino)propan-1-ol; 2-[(3-imidazol-1-yl-propylamino)-methyl]-1,4-diaminobenzene; 2-{[(tetrahydrofuran-2-yl-methyl)amino]methyl}-1,4-diaminobenzene; 4-(2,5-diaminobenzylamino)aniline; 3-(2,5-diaminobenzylamino)phenol; 5-(2,5-diaminobenzylamino)-2-methylphenol; 2-[(2-dimethylaminoethylamino)-methyl]-1,4-diaminobenzene; 4-(2,5-diaminobenzylamino)butan-1-ol; 2-[(3-ethoxypropylamino)methyl]-1,4-diaminobenzene; 2-[(3-methoxy-phenylamino)-methyl]-1,4-diaminobenzene; 2-[(4-chlorophenylamino)methyl]-1,4-diaminobenzene; 2-[(cyclopropyl-methylamino)methyl]-1,4-diaminobenzene; 2-(2,5-diaminobenzylamino)-4-nitrophenol; 2-[(4-chlorobenzylamino)methyl]-1,4-diaminobenzene; 2-[(2,5-diaminobenzyl)methylamino] ethanol; 2-[(2,5-diamino-benzyl)ethylamino]ethanol; 2-{[(pyridin-4-yl-methyl)amino]methyl}-1,4-diaminobenzene; 1-[3-(2,5-diaminobenzylamino)propyl]pyrrolidin-2-one; 2-(4-amino-2-methylphenyl)aminomethyl-1,4-diaminobenzene; 2-(4-amino-3-methylphenyl) aminomethyl-1,4-diaminobenzene; 2-[5-amino-2-(2,5-diamino-benzylamino)phenyl]ethanol; 2-(3-aminophenyl) aminomethyl -1,4-diaminobenzene; 4-[2-(2,5-diaminobenzylamino)ethyl]benzenesulfonamide; 2-[4-amino-2-(2,5-diaminobenzylamino)phenoxy]ethanol; 2-[(2,5-diaminobenzyl)-(2-hydroxy-ethyl)amino]ethanol; [1-(2,5-diaminobenzyl)pyrrolidin-2-yl]-methanol; 1-(2,5-diaminobenzyl)pyrrolidin-3-ol; 1-(2,5-diaminobenzyl)-pyrrolidin-2-carboxylic acid amide; 1-(2,5-diaminobenzyl) piperidin-3-ol; 2-(2,5-diamino-benzylamino)-propan-1,3-diol; 2-(2,5-diaminobenzylamino)-3-hydroxypropionamide; 2-(2,5-diaminobenzylamino)succinic acid; 2-cyclopropylaminomethyl-1,4-diaminobenzene; 2-(2,5-diaminobenzylamino)ethanol; (2,5-diaminobenzylamino) acetic acid; 4-(2,5-diaminobenzylamino)phenol; 2-(benzo [1,3]dioxol-5-yl-aminomethyl)-1,4-diaminobenzene; [(2,5-diaminobenzyl)methyl-amino]acetonitrile; 2-pentyl-aminomethyl-1,4-diaminobenzene; 2-[(3-dimethylaminopropylamino)-methyl]-1,4-diaminobenzene; 2-{[2-(5-nitropyridin-2-yl-amino)ethylamino]-methyl}-1,4-diaminobenzene; 2-[(2-aminoethylamino)methyl]-1,4-diaminobenzene; 3-[2-(2,5-diaminobenzylamino)-1-hydroxyethyl]phenol; 2-[(4-methyl-pyridin-2-yl-amino) methyl]-1,4-diaminobenzene; 2-(2,5-diaminobenzyl)-1- methyl-1,2,3,4-tetrahydroisoquinolin-6,7-diol; 2-(2,5-diamino-benzylamino)-4-methylsulfanyl-butyric acid; 1-(2,5-diaminobenzyl)pyrrolidin-2-carboxylic acid; 2-phenylamino-methyl-1,4-diaminobenzene; 2-(4-dimethylamino-phenylaminomethyl-1,4-diaminobenzene; 1-[3-(2,5-diaminobenzylamino)phenyl]ethanol; 1-[4-(2,5-diaminobenzylamino)-phenyl]ethanol; 1-[2-(2,5-diaminobenzylamino)-phenyl]ethanol; 2-[(3,4-dimethoxyphenylamino)methyl]-1,4-diaminobenzene; 2-[(3-fluoro-2-methoxy-phenylamino)-methyl]-1,4-diaminobenzene; 4-chloro-2-(2,5-diaminobenzylamino)-phenol; 2-[(4-trifluoromethyl-phenylamino)-methyl]-1,4-diamino-benzene; 2-(p-tolylaminomethyl)-1,4-diaminobenzene; $N^4$-dihydroxypropyl-2-(di(hydroxyethyl)aminomethyl)-1,4-diaminobenzene; $N^4$-dihydroxypropyl-2-(hydroxyethylaminomethyl)-1,4-diaminobenzene; $N^4$-dihydroxypropyl-2-(methylaminomethyl)-1,4-diaminobenzene; $N^4$-hydroxyethyl-2-(di(hydroxyethyl)aminomethyl)-1,4-diaminobenzene; $N^4$-hydroxyethyl-2-(hydroxyethylaminomethyl)-1,4-diaminobenzene; $N^4$-hydroxyethyl-2-(methylaminomethyl)-1,4-diaminobenzene; $N^4,N^4$-bis-(hydroxyethyl)-2-(di(hydroxyethyl)aminomethyl)-1,4-diaminobenzene; $N^4,N^4$-bis-(hydroxyethyl)-2-(hydroxyethylaminomethyl)-1,4-diaminobenzene; $N^4,N^4$-bis-(hydroxyethyl)-2-(methylaminomethyl)-1,4-diaminobenzene; $N^1$-dihydroxypropyl-2-(di(hydroxyethyl)aminomethyl)-1,4-diaminobenzene; $N^1$-dihydroxypropyl-2-(hydroxyethylaminomethyl)-1,4-diaminobenzene; $N^1$-dihydroxypropyl-2-(methylaminomethyl)-1,4-diaminobenzene; $N^1$-hydroxyethyl-2-(di(hydroxyethyl)aminomethyl)-1,4-diaminobenzene; $N^1$-hydroxyethyl-2-(hydroxyethylaminomethyl)-1,4-diamino-benzene; $N^1$-hydroxyethyl-2-(methylaminomethyl)-1,4-diaminobenzene; $N^1,N^1$-bis-(hydroxyethyl)-2-(di(hydroxyethyl)aminomethyl)-1,4-diaminobenzene; $N^1,N^1$-bis-(hydroxyethyl)-2-(hydroxyethylaminomethyl)-1,4-diaminobenzene; $N^1,N^1$-bis(hydroxyethyl)-2-(methylaminomethyl)-1,4-diaminobenzene; 2-((2-aminophenylamino)methyl)-1,4-diaminobenzene; 2-((2-hydroxyphenylamino)methyl)-1,4-diaminobenzene; 2-((2-dimethylaminophenylamino)-methyl)-1,4-diaminobenzene; 2-((2-methylphenylamino)methyl)-1,4-diaminobenzene; 2-((2-trifluoromethylphenylamino)methyl)-1,4-diaminobenzene; 2-((3-dimethylaminophenylamino)methyl)-1,4-diaminobenzene; 2-((3-methylphenylamino)methyl)-1,4-diaminobenzene; 2-((3-trifluoromethylphenylamino)methyl)-1,4-diaminobenzene; 2-((2-bromophenylamino)methyl)-1,4-diaminobenzene; 2-((2-cyanophenylamino)methyl)-1,4-diaminobenzene; 2-((2-fluorophenylamino)methyl)-1,4-diaminobenzene; 2-((2-methoxyphenylamino)methyl)-1,4-diaminobenzene; 2-((2-nitrophenylamino)methyl)-1,4-diaminobenzene; 2-((3-bromophenylamino)methyl)-1,4-diaminobenzene; 2-((3-cyanophenylamino)methyl)-1,4-diaminobenzene; 2-((3-fluorophenylamino)-methyl)-1,4-diaminobenzene; 2-((3-methoxyphenylamino)methyl)-1,4-diaminobenzene; 2-((3-nitrophenylamino)methyl)-1,4-diaminobenzene; 2-((4-bromophenylamino)methyl)-1,4-diaminobenzene; 2-((4-cyanophenylamino)-methyl)-1,4-diaminobenzene; 2-((4-fluorophenylamino)methyl)-1,4-diaminobenzene; 2-((4-methoxyphenylamino)methyl)-1,4-diaminobenzene; 2-((4-nitrophenylamino)methyl)-1,4-diaminobenzene; 2-((2-(1,3-dihydroxypropyl)aminophenylamino)-methyl)-1,4-diaminobenzene; 2-((2-di(hydroxyethyl)aminophenylamino)methyl)-1,4-diaminobenzene; 2-((2-hydroxyethylaminophenylamino)methyl)-1,4-diaminobenzene; 2-((2-pyrrolidin-phenylamino)methyl)-1,4-diaminobenzene 2-((3-(1,3-dihydroxypropyl)aminophenylamino)methyl)-1,4-diaminobenzene; 2-((3-di(hydroxyethyl)aminophenylamino)methyl)-1,4-diaminobenzene; 2-((3-hydroxyethylaminophenylamino)methyl)-1,4-diaminobenzene; 2-((3-pyrrolidin-phenylamino)methyl)-1,4-diaminobenzene; 2-((4-(1,3-dihydroxypropyl)aminophenylamino)methyl)-1,4-diaminobenzene; 2-((4-di(hydroxyethyl)aminophenylamino)methyl)-1,4-diaminobenzene; 2-((4-hydroxyethylaminophenylamino)methyl)-1,4-diaminobenzene; 2-((4-pyrrolidin-phenylamino)methyl)-1,4-diaminobenzene; 2-((4-amino-2-(2-hydroxyethoxy)phenylamino)methyl)-1,4-diaminobenzene; 2-((4-amino-2-chlorophenylamino)methyl)-1,4-diaminobenzene; 2-((4-amino-2-hydroxyphenylamino)methyl)-1,4-diaminobenzene; 2-((4-amino-2-methoxyphenylamino)methyl)-1,4-diaminobenzene; 2-((4-amino-3-(2-hydroxyethoxy)phenylamino)-methyl)-1,4-diaminobenzene; 2-((4-amino-3-chlorophenylamino)methyl)-1,4-diaminobenzene; 2-((4-amino-3-hydroxyphenylamino)methyl)-1,4-diaminobenzene; 2-((4-amino-3-methoxyphenylamino)-methyl)-1,4-diaminobenzene; 2-((3,4-diamino-phenylamino)methyl)-1,4-diaminobenzene; 2-((2,4-diaminophenylamino)methyl)-1,4-diaminobenzene; $N^4$-dihydroxypropyl-2-((4-aminophenylamino)methyl)-1,4-diaminobenzene; $N^4$-dihydroxypropyl-2-(phenylaminomethyl)-1,4-diaminobenzene; $N^4$-dihydroxypropyl-2-((4-di(hydroxyethyl)aminophenylamino)-methyl)-1,4-diaminobenzene; $N^4$-dihydroxypropyl-2-((4-hydroxyethylaminophenylamino)methyl)-1,4-diaminobenzene; $N^4$-hydroxyethyl-2-((4-aminophenylamino)methyl)-1,4-diaminobenzene; $N^4$-hydroxyethyl-2-(phenylaminomethyl)-1,4-diaminobenzene; $N^4$-hydroxyethyl-2-((4-di(hydroxyethyl)aminophenylamino)methyl)-1,4-diaminobenzene; $N^4$-hydroxyethyl-2-((4-hydroxyethylaminophenylamino)methyl)-1,4-diaminobenzene; $N^4,N^4$-bis-(hydroxyethyl)-2-(4-aminophenylamino)-methyl)-1,4-diaminobenzene; $N^4,N^4$-bis-(hydroxyethyl)-2-phenylaminomethyl)-1,4-diaminobenzene; $N^4,N^4$-bis-(hydroxyethyl)-2-(4-di(hydroxyethyl)aminophenylamino)methyl)-1,4-diaminobenzene; $N^4,N^4$-bis-(hydroxyethyl)-2-(4-hydroxyethylamino-phenylamino)methyl)-1,4-diaminobenzene; $N^1$-dihydroxypropyl-2-((4-aminophenylamino)methyl)-1,4-diaminobenzene; $N^1$-dihydroxypropyl-2-(phenylaminomethyl)-1,4-diaminobenzene; $N^1$-dihydroxypropyl-2-((4-di(hydroxyethyl)aminophenylamino)methyl)-1,4-diaminobenzene; $N^1$-dihydroxypropyl-2-((4-hydroxyethylaminophenylamino)methyl)-1,4-diaminobenzene; $N^1$-hydroxyethyl-2-((4-aminophenylamino)methyl)-1,4-diaminobenzene; $N^1$-hydroxyethyl-2-(phenylaminomethyl)-1,4-diaminobenzene; $N^1$-hydroxyethyl-2-((4-di(hydroxyethyl)aminophenylamino)methyl)-1,4-diaminobenzene; $N^1$-hydroxyethyl-2-((4-hydroxyethylaminophenylamino)methyl)-1,4-diaminobenzene; $N^1,N^1$-bis-(hydroxyethyl)-2-(4-aminophenylamino)methyl)-1,4-diaminobenzene; $N^1,N^1$-bis-(hydroxyethyl)-2-phenylaminomethyl)-1,4-diaminobenzene; $N^1,N^1$-bis-(hydroxyethyl)-2-(4-di(hydroxyethyl)aminophenylamino)methyl)-1,4-diaminobenzene; $N^1,N^1$-bis-(hydroxyethyl)-2-(4-hydroxyethylaminophenylamino)methyl)-1,4-diaminobenzene; 2-[5-amino-4-(2,5-diaminophenylamino)-pyrazol-1-yl]ethanol; $N^2$-(5-amino-1-methyl-1H-pyrazol-4- yl)-1,2,4-triaminobenzene; N²-(5-amino-1-isopropyl-1H-pyrazol-4-yl)-1,2,4-triaminobenzene and N²-(5-amino-1,3-dimethyl-1H-pyrazol-4-yl)-1,2,4-triaminobenzene.

The preferred compounds of formula (I) are those compounds, in which (i) one or more groups R5 and R8 are hydrogen and/or (ii) R1, R2, R3 and R4 simultaneously represent hydrogen and/or (iii) R6 represents a methyl group or a C₁–C₄-hydroxyalkyl group and R7 represents a C₁–C₄-hydroxyalkyl group and/or (iv) R6 represents hydrogen and R7 represents a C₁–C₄-hydroxyalkyl group, a substituted pyridyl group, a substituted phenyl group, a substituted pyrazoyl group or a group of the following formula:

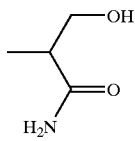

and/or (v) R6 and R7 represent an aliphatic ring of the formula:

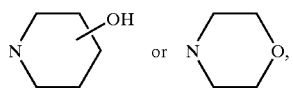

Particularly the following compounds are preferred examples of the compounds of formula (I): 2-(2,3-dihydroxypropyl)aminomethyl-1,4-diaminobenzene; 2-[(2-aminoethylamino)methyl]-1,4-diaminobenzene; 2-[(2-hydroxyethylamino)methyl]-1,4-diaminobenzene; 2-[(2,5-diaminobenzyl)methylamino]ethanol; 2-(2,5-diaminobenzylamino)-propan-1-ol; 2-[(2,5-diaminobenzyl)-(2-hydroxyethyl)amino]ethanol; [1-(2,5-diaminobenzyl)pyrrolidin-2-yl]methanol; 1-(2,5-diaminobenzyl)-pyrrolidin-2-carbamide; 2-[(4-methylpyridin-2-yl-amino)methyl]-1,4-diaminobenzene; 2-((2-aminophenylamino)methyl)-1,4-diaminobenzene; 2-((2-chlorophenylamino)methyl)-1,4-diaminobenzene; 2-((2-dimethylaminophenyl-amino)methyl)-1,4-diaminobenzene; 2-((2-fluorophenylamino)methyl)-1,4-diaminobenzene; 2-((2-hydroxyethylaminophenylamino)methyl)-1,4-diaminobenzene; 2-((2-N,N-bis-(hydroxyethyl)aminophenylamino)methyl)-1,4-diaminobenzene; 2-((2-pyrrolidinphenylamino)methyl)-1,4-diaminobenzene; 2-((3-aminophenylamino)methyl)-1,4-diaminobenzene; 2-((3-chlorophenylamino)methyl)-1,4-diaminobenzene; 2-((3-dimethylaminophenylamino)methyl)-1,4-diaminobenzene; 2-((3-fluorophenylamino)methyl)-1,4-diaminobenzene; 2-((3-hydroxyethylaminophenylamino)methyl)-1,4-diamino-benzene; 2-((3-N,N-bis-(hydroxyethyl)aminophenylamino)methyl)-1,4-diaminobenzene; 2-((3-pyrrolidin-phenylamino)methyl)-1,4-diaminobenzene; 2-((4-aminophenylamino)methyl)-1,4-diaminobenzene; 2-((4-chlorophenylamino)methyl)-1,4-diaminobenzene; 2-((4-dimethylaminophenylamino)methyl)-1,4-diaminobenzene; 2-((4-fluorophenylamino)methyl)-1,4-diaminobenzene; 2-((4-hydroxyethylaminophenylamino)methyl)-1,4-diaminobenzene; 2-((4-N,N-bis-(hydroxyethyl)aminophenylamino)methyl)-1,4-diaminobenzene; 2-((4-pyrrolidinphenylamino)methyl)-1,4-diaminobenzene; 2-((2-(2-hydroxy)-ethoxy-4-aminophenylamino)methyl)-1,4-diaminobenzene; 2-((2-amino-4-aminophenylamino)methyl)-1,4-diaminobenzene; 2-((2-chloro-4-aminophenylamino)methyl)-1,4-diaminobenzene; 2-((2-hydroxy-4-aminophenylamino)methyl)-1,4-diaminobenzene; 2-((2-hydroxyethylamino-4-aminophenylamino)methyl)-1,4-diaminobenzene; 2-((2-methyl-4-aminophenylamino)methyl)-1,4-diaminobenzene; 2-((3-(2-hydroxy)-ethoxy-4-aminophenylamino)methyl)-1,4-diaminobenzene; 2-((3-amino-4-aminophenylamino)methyl)-1,4-diaminobenzene; 2-((3-chloro-4-aminophenylamino)methyl)-1,4-diaminobenzene; 2-((3-hydroxy-4-aminophenylamino)methyl)-1,4-diaminobenzene; 2-((3-hydroxyethylamino-4-aminophenylamino)methyl)-1,4-diaminobenzene; 2-((3-methyl-4-aminophenylamino)-methyl)-1,4-diaminobenzene; 2-((2-(2-hydroxy)ethoxyphenylamino)methyl)-1,4-diaminobenzene; 2-((2-hydroxyphenylamino)methyl)-1,4-diaminobenzene; 2-((3-(2-hydroxy)ethoxyphenylamino)methyl)-1,4-diaminobenzene; 2-((3-hydroxyphenylamino)-methyl)-1,4diaminobenzene; 2-((4-(2-hydroxy)-ethoxy-phenyl-amino)methyl)-1,4-diaminobenzene; 2-((4-hydroxyphenylamino)methyl)-1,4-diaminobenzene; 2-(phenylamino)methyl-1,4-diaminobenzene; 2-[5-amino-4-(2,5-diaminophenylamino)-pyrazol-1-yl]ethanol; N²-(5-amino-1-methyl-1H-pyrazol-4-yl)-1,2,4-triaminobenzene; N²-(5-amino-1-isopropyl-1H-pyrazol-4-yl)-1,2,4-triaminobenzene and N²-(5-amino-1,3-dimethyl-1H-pyrazol-4-yl)-1,2,4-triaminobenzene.

The compounds of formula I can be employed both as free bases and also in the form of their physiologically compatible salts with inorganic or organic acids, such as hydrochloric acid, sulfuric acid, phosphoric acid, acetic acid, propionic acid, lactic acid or citric acid.

The method of making the substituted diaminobenzene derivatives according to formula (I) can occur using known synthetic methods. The synthesis of the compounds according to the invention, for example, can occur by the following methods: Either (a) by performing a reductive amination of a substituted benzene of formula (V):

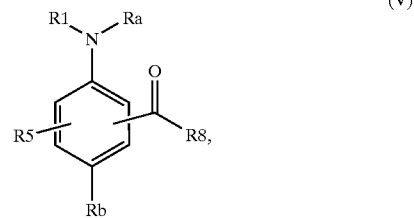

in which Ra has the significance of a protective group, for example as described in the chapter, "Protective Groups" in Organic Synthesis, Chapter 7, Wiley Interscience, 1991; Rb represents NR1Ra or NR1R2; by reacting the compound of formula (V) with an amine of formula HNR6R7, wherein R1, R2, R5, R6, R7 and R8 have the same significance as in formula (I) above and subsequently splitting off the protective group; or (b) by substitution of a substituted benzene of formula (VI):

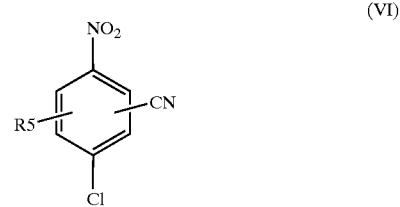

with an amine of formula HNR1R2, reduction of the nitrile group, subsequent alkylation of the amino group with a compound of formula XR6 and/or XR7, and finally reduction of the nitro group, wherein R1, R2, R5, R6 and R7 have the same significance as in the above formula (I) and X represents a halogen atom.

The substituted 2-aminoalkyl-1,4-diaminobenzene compounds according to formula (I) are soluble in water and produce colors with a higher intensity and better fastness, especially light-fastness, wash-fastness and rubbing-fastness, than prior art developer compounds. The substituted 2-aminoalkyl-1,4-diaminobenzene compounds according to formula (I) have outstanding storage stability, especially as components of a subsequently described oxidation dye precursor composition.

The subject matter of the present invention also includes a composition for oxidative dyeing of keratin fibers, for example hairs, fur, fibers or wool, especially human hair, comprising a combination of coupler substance and developer substances, which contain at least one substituted 2-aminoalkyl-1,4-diamino-benzene compound of formula (I).

The at least one 2-aminoalkyl-1,4-diaminobenzene derivative compound of formula (I) is present in the oxidation dye precursor composition according to the invention in an amount of about 0.005 to 20 percent by weight, however an amount of about 0.01 to 8.0 percent by weight is preferred and 0.1 to 5.0 percent by weight is particularly preferred.

The coupler substance preferably can be 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di(2-hydroxyethoxy)-benzene, 1-(2-aminoethoxy)-2,4-diaminobenzene, 2-amino-1-(2-hydroxyethoxy)-4-methylaminobenzene, 2,4-diaminophenoxyacetic acid, 3-[(di(2-hydroxyethyl)-amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-amino-ethyl)amino]aniline, 1,3-di(2,4-diaminophenoxy)propane, di(2,4-diaminophenoxy)methane, 1,3-diamino-2,4-dimethoxy-benzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methyphenol, 5-amino-4-ethoxy-2-methylphenol, 3-amino-2,4-dicholorophenol, 5-amino-2,4-dichlorophenol, 3-amino-2-methylphenol, 3-amino-2-chloro-6-methylphenol, 3-aminophenol, 2-{(3-hydroxyphenyl)amino]-acetamide, 5-[(2-hydroxyethyl)amino]-2-methylphenol, 3-[(2-hydroxyethyl)-aminophenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methyl-phenol, 2-amino-3-hydroxypyridine, 5-amino-4-chloro-2-methyl-phenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro- 1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxy-ethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxy-indole, 5,6-dihydroxyindoline, 5-hydroxyindole, 6-hydroxy-indole, 7-hydroxyindole and 2,3-indolindione.

Although the advantageous properties of the above-described substituted 2-aminoalkyl-1,4-diaminobenzene compounds of formula (I) can obviously be obtained when the diaminobenzene derivative compounds of formula (I) are used alone, it is understandably also possible to use the 2-aminoalkyl-1,4-diamino-benzene compounds of formula (I) together with known developer substances, such as 1,4-diaminobenzene, 2,5-diaminotoluene, 2,5-diaminophenyl-ethyl alcohol, 4-aminophenol and its derivatives, especially 4-amino-3-methylphenol, 4,5-diamino-1-(2-hydroxyethyl)pyrazole or tetraaminopyrimidines.

The coupler and developer substances can be contained in the oxidation dye precursor compositions according to the invention individually, or in mixtures with each other. The coupler substances and developer substances are contained in the dye precursor composition according to the invention (relative to the total amount of the dye precursor composition) in an amount of from about 0.005 to 20 percent by weight respectively. However an amount of from about 0.01 to 5.0 percent by weight is preferable and from 0.1 to 2.5 percent by weight is especially preferably.

The total amount of the combination of developer and coupler substances in the oxidation dye precursor composition described here is preferably from about 0.01 to 20 percent by weight, especially preferably from about 0.02 to 10 percent by weight, and most preferably from 0.2 to 6.0 percent by weight. The developer and coupler substances are used generally in equimolar amounts, however it is not disadvantageous when the developer substances are present in a certain excess or deficiency.

The dye compositions according to the invention can also contain certain other dye ingredients, for example 6-amino-2-methylphenol and 2-amino-5-methylphenol, as well as conventional direct-dyeing dye compounds, such as triphenylmethane dye compounds, such as 4-[(4'-aminophenyl)-(4'-imino-2",5"-cyclohexadien-1"-yliden)-methyl]-2-methylaminobenzene monohydrochloride (C.I. 42 510) and 4-[(4'-amino-3'-methylphenyl)-(4"-imino-2",5"-cyclohexadien-1"-yliden)methyl]-2-methylaminobenzene monohydrochloride (C.I. 42 520); aromatic nitro dye compounds, such as 4-(2'-hydroxyethyl)aminonitrotoluene, 2-amino-4,6-dinitrophenol, 2-amino-5-(2'-hydroxyethyl) aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro6-nitro-phenol and 1-[(2'-ureidoethyl)amino-4-nitrobenzene; azo dye compounds, such as 6-[(4'-aminophenyl)azo]-5-hydroxy-napththalen-1-sulfonic acid sodium salt (C.I 14 805) and dispersion dye compounds, such as 1,4-diaminoanthraquinone and 1,4,5,8-tetraaminoanthraquinone. These additional dye compounds can be contained in the oxidation dye precursor composition of the invention in an amount of from about 0.1 to 4.0 percent by weight.

Understandably the coupler substances and the developer substances as well as the other dye compounds, in so far as they are bases, can also be used in the form of their physiologically compatible salts with organic or inorganic acids, such as hydrochloric acid or sulfuric acid, or, in so far as they have aromatic OH groups, in the form of their salts with bases, such as alkali phenolates.

Moreover cosmetic additive ingredients, which are commonly used in compositions for dyeing hair, can be used in the oxidation dye precursor compositions according to the invention, for example antioxidants, such as ascorbic acid, thioglycolic acid or sodium sulfite, and perfume oils, complex formers, wetting agents, emulsifiers, thickeners and care materials. The form of the dye compositions according to the invention can be, for example, a solution, especially an aqueous or aqueous-alcoholic solution. However the form that is particularly preferred is a cream, gel or an emulsion. Its composition is a mixture of the dye ingredients with the conventional cosmetic additive ingredients suitable for the particular preparation.

Conventional cosmetic additive ingredients in solutions, creams, emulsion or gels include, for example, solvents, such as water, lower aliphatic alcohols, such as ethanol, propanol or isopropanol, glycerol or glycols, such as 1,2-propylene glycol, wetting agents or emulsifiers from the classes of anionic, cationic, amphoteric or nonionic surfactant compounds, such as fatty alcohol sulfates, ethoxylated fatty alcohol sulfates, alkylsulfonates, alkylbenzenesulfonates, alkyltrimethylammonium salts, aklylbetaines, ethoxylated fatty alcohols, ethoxylated nonylphenols, fatty acid alkanol amides and ethoxylated fatty acid esters; thickeners, such as higher fatty alcohols, starches, cellulose derivatives, petrolatum, paraffin oil and fatty acids, as well as care materials, such as cationic resins, lanolin derivatives, cholesterol, pantothenic acids and betaine. The above-mentioned conventional cosmetic ingredients are used in amounts suitable for their purposes. For example the wetting agents and emulsifiers are used in concentrations of from about 0.5 to 30 percent by weight, the thickeners are used in an amount of from about 0.1 to 25 percent by weight and the care materials are used in concentrations of from about 0.1 to 5.0 percent by weight.

The oxidation dye precursor compositions according to the invention can be weakly acidic, neutral or alkaline according to their composition. These compositions preferably have pH values of from 6.8 to 11.5. Their pH can be adjusted in the basic range with ammonia. Also organic amines can be used for this purpose, including monoethanolamine and triethanolamine, or also inorganic bases, such as sodium hydroxide and potassium hydroxide. Inorganic or organic acids can be used for adjusting the pH in the acid range, for example phosphoric acid, acetic acid, citric acid or tartaric acid.

In order to use the oxidation hair dye precursor composition for dyeing hair one mixes the above-described compositions according to the invention with an oxidizing agent immediately prior to use and applies a sufficient amount of the ready-to-apply mixture to the hair, according to the hair abundance, generally from about 60 to 200 grams.

Principally hydrogen peroxide, or its addition compounds with urea, melamine, sodium borate or sodium carbonate, can be used in the form of a 3 to 12 percent, preferably 6 percent, aqueous solution as the oxidizing agent for developing the hair dye. Air oxygen can also be used as the oxidizing agent. If a 6 percent hydrogen peroxide solution is used as oxidizing agent, the weight ratio of hair dye composition and oxidizing agent is 5:1 to 1:2, but preferably 1:1. Larger amounts of oxidizing agent are used above all with larger dye concentrations in the oxidation dye precursor composition, or when at the same time a strong bleaching of the hair is desired. The mixture of the oxidizing agent and the oxidation dye precursor composition of the invention is allowed to act on the hair for about 10 to 45 minutes, preferably 30 minutes, at 15 to 65 degrees Celsius, the hair is rinsed with water and dried. If necessary it is washed with a shampoo and eventually after-rinsed with a weak organic acid, such as citric acid or tartaric acid. Subsequently the hair is dried.

The oxidation hair dye precursor compositions according to the invention with a content of the substituted 2-aminoalkyl-1,4-diaminobenzene compounds of formula (I) as developer substances permit hair dyeing with outstanding color fastness, especially light fastness, fastness to washing and fastness to rubbing. The dye precursor compositions according to the invention provide a broad palette of different color shades, which extend from blond to brown, purple, violet to blue and black shades, according to the type and composition of the dye compounds in it. Particularly the color shades produced have outstanding color intensity. The very good dyeing properties of the compositions according to the invention include the production of good color coverage and dyeing of gray, chemically not-previously damaged hair without problems.

The following examples should serve to illustrate the invention, but details present in these examples should not be considered as further limiting the following appended claims, unless they are explicitly included in the following appended claims.

EXAMPLES

Example 1

Synthesis of 2-(aminomethyl)-1,4-diaminobenzene Compounds

General Synthetic Recipe

A. Synthesis of 2,5-bis.-tert.-butyloxycarbonylaminobromobenzene 15.65 g (0.07 mol)bromo-p-phenylenediamine hydrochloride and 32.7 g (0.15 mol)di-tert.-butyl-dicarbonate are dissolved in a mixture of 250 ml 2N sodium hydroxide and 250 ml trifluorotoluene and heated at 45° C. This reaction mixture is stirred for 3 days. Then 30 g (0.14 mol) di-tert.-butyl dicarbonate are gradually added. Subsequently the organic layer is separated and the aqueous phase is extracted twice with 100 ml dichloromethane. The combined extracts are evaporated to dryness and the residue is taken up in 200 ml of hexane. The precipitate is filtered and washed with 50 ml hexane. 18.6 g (82% of theoretical) of 2,5-bis-tert.-butyloxycarbonylaminobromobenzene is obtained with a melting point of 130° C.

B. Synthesis of N-(4-tert.-butyloxycarbonylamino-2-formylPhenyl)carbamic acid-tert. butylester 3.3 g (0.01 mol) 2,5-bis-tert.-butyloxycarbonylaminobromobenzene from step A are dissolved in 100 ml of water-free tetrahydrofuran under argon. 17 ml of a 1.6 molar etheric methyl lithium solution (0.03 mol) are gradually added. The reaction mixture is cooled to −20° C., 7 ml of a 1.5 molar tert.-butyl lithium solution (0.01 mol) are gradually added. After the addition has ended the solution is stirred for 30 minutes at the given temperature. Subsequently 1.2 g of dimethyl formamide (0.02 mol) are added and the reaction mixture is stirred for one hour at −20° C. After slowly heating to room temperature the reaction mixture is hydrolyzed with water and then poured into ether, the aqueous phase is extracted with ether and then the organic phase is dried over magnesium sulfate. The solvent is distilled away in a rotary evaporator and the residue is purified on silica gel with a petroleum ether/ethyl acetate solvent (9/1).

C. Synthesis of Substituted 2-aminomethyl-1,4-diaminobenzene Compounds 0.033 g (0.0001 mol) N-(4-tert.-butyloxycarbonylamino-2-formylphenyl)-carbamic acid-tert.-butyl ester from step B and 0.00015 mol of the corresponding amines are dissolved in 1,2-dichloroethane. Subsequently 0.1 ml of an acetic acid solution (1M in 1,2-dichloroethane) and 0.06 g NaBH(OAc)$_3$ (0.0003 mol) are added and the reaction mixture is stirred from 5 to 15 hours at room temperature.

After ending the reaction the reaction mixture is poured into 10 ml of ethyl acetate, the organic phase is extracted with sodium hydrogen carbonate and then dried with magnesium sulfate. The solvent is distilled off in a rotary evaporator and the residue is purified with petroleum ether/ethyl acetate (9:1). The product thus obtained is heated in 4 ml ethanol at 50° C.

Subsequently 1.5 ml of a 2.9 molar ethanolic hydrochloric acid solution are added drop-wise. The precipitate is filtered off, washed twice with 1 ml ethanol and then dried.

a1. 2-ethylamino-1,4-diaminobenzene hydrochloride
Amine Used: ethylamine
Yield: 0.025 g (91% of theory) Mass Spectrum MH$^+$ 166(100)

b1. 2-(isopropylaminomethyl)-1,4-diaminobenzene hydrochloride
Amine Used: isopropylamine
Yield: 0.017 g (59% of theory) Mass Spectrum MH$^+$ 180(100)

c1. 2-propylaminomethyl-1,4-diaminobenzene hydrochloride
Amine Used: propylamine
Yield: 0.025 g (87% of theory) Mass Spectrum MH$^+$ 180(100)

d1. 2-pyrrolidin-1-ylmethyl-1,4-diaminobenzene hydrochloride
Amine Used: pyrrolidine
Yield: 0.025 g (83% of theory) Mass Spectrum MH$^+$ 192(100)

e1. 2-[(2-methoxyethylamino)methyl]-1,4-diaminobenzene hydrochloride
Amine Used: 2-methoxyethylamine
Yield: 0.025 g (82% of theory) Mass Spectrum MH$^+$ 196(100)

f1. 2-morpholin-4-ylmethyl-1,4-diaminobenzene hydrochloride
Amine Used: morpholine
Yield: 0.025 g (79% of theory) Mass Spectrum MH$^+$ 208(100)

g1. 2-(2,5-diaminobenzylamino)butan-1-ol hydrochloride
Amine Used: 2-amino-1-butanol
Yield. 0.025 g (78% of theory) Mass Spectrum MH$^+$ 210(100)

h1. 2-{[(furan-2-ylmethyl)amino]methyl}-1,4-diaminobenzene hydrochloride
Amine Used: furfurylamine
Yield. 0.025 g (76% of theory) Mass Spectrum MH$^+$ 218(100)

i1. N-(2,5-diaminobenzyl)-O,N-dimethylhydroxylamine hydrochloride
Amine Used: O,N-dimethylhydroxylamine
Yield: 0.025 g (86% of theory) Mass Spectrum MH$^+$ 182(100)

j1. 2-(4-methylpiperazin-1-ylmethyl)-1,4-diaminobenzene hydrochloride
Amine Used: 4-methylpiperazine
Yield: 0.025 g (68% of theory) Mass Spectrum MH$^+$ 221 (100)

k1. 1-(2,5-diaminobenzyl)piperidin-4-ol hydrochloride
Amine Used: 4-hydroxypiperidine
Yield: 0.025 g (76% of theory) Mass Spectrum MH$^+$ 222(100)

l1. N-[2-(2,5-diaminobenzylamino)ethyl]acetamide hydrochloride N-acetylethylenediamine
Amine Used: ethylamine
Yield: 0.025 g (75% of theory) Mass Spectrum MH$^+$ 223(100)

m1. 2-[(2-morpholin4-yl-ethylamino)methyl]-1,4-diaminobenzene hydrochloride
Amine Used: 4-(2-ethylamino)morpholine
Yield: 0.025 g (63% of theory) Mass Spectrum MH$^+$ 251 (100)

n1. 2-allylaminomethyl-1,4-diaminobenzene hydrochloride
Amine Used: allylamine
Yield: 0.025 g (87% of theory) Mass Spectrum MH$^+$ 178(100)

o1. 2-(2,5-diaminobenzylamino)propan-1-ol hydrochloride
Amine Used: 2-aminopropanol
Yield: 0.025 g (82% of theory) Mass Spectrum MH$^+$ 196(100)

p1. 2-[(3-imidazol-1-ylpropylamino)methyl]-1,4-diaminobenzene hydrochloride
Amine Used: 1-(3-aminopropyl)imidazole
Yield: 0.025 g (64% of theory) Mass Spectrum MH$^+$ 246(100)

q1. 2-{[(tetrahydrofuran-2-ylmethyl)amino]methyl}-1,4-diaminobenzene hydrochloride
Amine Used: tetrahydrofurfurylamine
Yield: 0.025 g (76% of theory) Mass Spectrum MH$^+$ 222(100)

r1. 4-(2,5-diaminobenzylamino)aniline hydrochloride
Amine Used: 4-tert.-butyloxycarbonylaminoaniline
Yield: 0.025 g (67% of theory) Mass Spectrum MH$^+$ 229(100)

s1. 3-(2,5-diaminobenzylamino)phenol hydrochloride
Amine Used: 3-aminophenol
Yield: 0.025 g (74% of theory) Mass Spectrum MH$^+$ 230(100)

t1. 5-(2,5-diaminobenzylamino)-2-methylphenol hydrochloride
Amine Used: 3-amino-6-methylphenol
Yield: 0.025 g (71% of theory) Mass Spectrum MH$^+$ 244(100)

u1. 2-[(2-dimethylaminoethylamino)methyl]-1,4-diaminobenzene hydrochloride
Amine Used: 2-dimethylaminoethylamine
Yield: 0.016 g (45% of theory) Mass Spectrum MH⁺ 209(100)

v1. 4-(2,5-diaminobenzylamino)butan-1-ol hydrochloride
Amine Used: 4-aminobutanol
Yield: 0.022 g (69% of theory) Mass Spectrum MH⁺ 210(100)

w1. 2-[(3-ethoxypropylamino)methyl]-1,4-diaminobenzene hydrochloride
Amine Used: 3-ethoxypropylamine
Yield: 0.025 g (75% of theory) Mass Spectrum MH⁺ 224(100)

x1. 2-[(3-methoxyphenylamino)methyl]-1,4-diaminobenzene hydrochloride
Amine Used: 3-methoxyaniline
Yield: 0.025 g (71% of theory) Mass Spectrum MH⁺ 244(100)

y1. 2-[(4-chlorophenylamino)methyl]-1,4-diaminobenzene hydrochloride
Amine Used: 4-chloroaniline
Yield: 0.025 g (70% of theory) Mass Spectrum MH⁺ 248(100)

z1. 2-[(cyclopropylmethylamino)methyl]-1,4-diaminobenzene hydrochloride
Amine Used: aminomethylcyclopropane
Yield: 0.017 g (56% of theory) Mass Spectrum MH⁺ 192(100)

a2. 2-(2,5-diaminobenzylamino)4-nitrophenol hydrochloride
Amine Used: 2-amino-4-nitrophenol
Yield: 0.025 g (65% of theory) Mass Spectrum MH⁺ 275(100)

b2. 2-[(4-chlorobenzylamino)methyl]-1,4-diaminobenzene hydrochloride
Amine Used: 4-chlorobenzylamine
Yield: 0.025 g (67% of theory) Mass Spectrum MH⁺ 262(100)

c2. 2-[(2,5-diaminobenzyl)methylamino]ethanol hydrochloride
Amine Used: 2-methylaminoethanol
Yield: 0.025 g (82% of theory) Mass Spectrum MH⁺ 196(100)

d2. 2-[(2,5-diaminobenzyl)ethylamino]ethanol hydrochloride
Amine Used: 2-ethylaminoethanol
Yield: 0.025 g (78% of theory) Mass Spectrum MH⁺ 210(100)

e2. 2-{[(pyridin-4-ylmethyl)amino]methyl}-1,4-diaminobenzene hydrochloride
Amine Used: 4-picolylamine
Yield: 0.025 g (67% of theory) Mass Spectrum MH⁺ 229(100)

f2. 1-[3-(2,5-diaminobenzylamino)propyl]pyrrolidin-2-one hydrochloride
Amine Used: 1-(3-aminopropyl)-2-pyrrolidone
Yield: 0.025 g (67% of theory) Mass Spectrum MH⁺ 263(100)

q2. 2-(4-amino-2-methylphenyl)aminomethyl-1,4-diaminobenzene hydrochloride and 2-(4-amino-3-methylphenyl)aminomethyl-1,4-diaminobenzene hydrochloride
Amines Used: 4-tert.-butyloxycarbonylamino-3-methylaniline and 4 tert.-butyloxycarbonylamino-2-methylaniline
Yield: 0.021 g (27% of theory) Mass Spectrum MH⁺ 243(100)

h2. 2-[5-amino-2-(2,5-diaminobenzylamino)phenyl]ethanol hydrochloride and 2-[2-amino-5-(2,5-diaminobenzylamino)phenyl]ethanol hydrochloride
Amines Used: 4-tert.-butyloxycarbonylamino-3-(2-hydroxyethyl)aniline and 4 tert.-butyloxycarbonylamino-2-(2-hydroxyethyl)aniline
Yield: 0.025 g (30% of theory) Mass Spectrum MH⁺ 273(100)

i2. 2-(3-aminophenyl)aminomethyl-1,4-diaminobenzene hydrochloride
Amine Used: 3-tert.-butyloxycarbonylaminoaniline
Yield: 0.025 g (67% of theory) Mass Spectrum MH⁺ 229(100)

j2. 4-[2-(2,5-diaminobenzylamino)ethyl]benzene sulfonamide hydrochloride
Amine Used: 4-(2-aminoethyl)benzene sulfonamide
Yield: 0.025 g (58% of theory) Mass Spectrum MH⁺ 321(100)

k2. 2-[4-amino-2-(2,5-diaminobenzylamino)phenoxy]ethanol hydrochloride
Amine Used: 4-tert.-butyloxycarbonylamino-2-amino-(2-hydroxy)ethoxybenzene
Yield: 0.025 g (58% of theory) Mass Spectrum MH⁺ 289(100)

l2. 2-[(2,5-diaminobenzyl)-(2-hydroxyethyl)amino]ethanol hydrochloride
Amine Used: diethanolamine
Yield: 0.025 g (75% of theory) Mass Spectrum MH⁺ 226(100)

m2. [1-(2,5-diaminobenzyl)pyrrolidin-2-yl]methanol hydrochloride
Amine Used: prolinol
Yield: 0.025 g (76% of theory) Mass Spectrum MH⁺ 222(100)

n2. 1-(2,5-diaminobenzyl)pyrrolidin-3-ol hydrochloride
Amine Used: 3-hydroxypyrrolidine
Yield: 0.025 g (79% of theory) Mass Spectrum MH⁺ 208(100)

o2. 1-(2,5-diaminobenzyl)pyrrolidin-2-carboxamide hydrochloride
Amine Used: prolinamide
Yield: 0.025 g (73% of theory) Mass Spectrum MH⁺ 235(100)

p2. 1-(2,5-diaminobenzyl)piperdin-3-ol hydrochloride
Amine Used: 3-hydroxypiperidine
  Yield: 0.025 g (76% of theory) Mass Spectrum MH$^+$ 222(100)

q2. 2-(2,5-diaminobenzylamino)propan-1,3-diol hydrochloride
Amine Used: 3-amino-1,2-propandiol
  Yield: 0.015 g (47% of theory) Mass Spectrum MH$^+$ 212(100)

r2. 2-(2,5-diaminobenzylamino)-3-hydroxypropionamide hydrochloride
Amine Used: 3-hydroxy-2-aminopropionamide
  Yield: 0.025 g (75% of theory) Mass Spectrum MH$^+$ 225(100)

s2. 2-(2,5-diaminobenzylamino)-succinic acid hydrochloride
Amine Used: aspargine
  Yield: 0.037 g (102% of theory) Mass Spectrum MH$^+$ 253 (100)

t2. 2-cyclopropylaminomethyl-1,4-diaminobenzene hydrochloride
Amine Used: cyclopropylamine
  Yield: 0.025 g (87% of theory) Mass Spectrum MH$^+$ 178(100)

u2. 2-(2,5-diaminobenzylamino)ethanol hydrochloride
Amine Used: ethanolamine
  Yield: 0.025 g (86% of theory) Mass Spectrum MH$^+$ 182(100)

v2. (2,5-diaminobenzylamino)acetic acid hydrochloride
Amine Used: glycine
  Yield: 0.025 g (82% of theory)

w2. 4-(2,5-diaminobenzylamino)phenol hydrochloride
Amine Used: 4-aminophenol
  Yield: 0.025 g (75% of theory) Mass Spectrum MH$^+$ 230(100)

x2. 2-(benzo[1,3]dioxol-5-ylaminomethyl)-1,4-diaminobenzene hydrochloride
Amine Used: 3,4-methylenedioxyaniline
  Yield: 0.025 g (68% of theory) Mass Spectrum MH$^+$ 258(100)

y2. [(2,5-diaminobenzyl)methylamino)acetonitrile hydrochloride
Amine Used: methylaminoacetonitrile
  Yield: 0.025 g (83% of theory) Mass Spectrum MH$^+$ 191 (100)

z2. 2-pentylaminomethyl-1,4-diaminobenzene hydrochloride
Amine Used: pentylamine
  Yield: 0.025 g (79% of theory) Mass Spectrum MH$^+$ 208(100)

a3. 2-[(3-dimethylaminopropylamino)methyl]-1,4-diaminobenzene hydrochloride
Amine Used: 3-dimethylaminopropylamine
  Yield: 0.025 g (68% of theory) Mass Spectrum MH$^+$ 223(100)

b3. 2-{[2-(5-nitropyridin-2-ylamino)ethylamino]methyl}1,4-diaminobenzene hydrochloride
Amine Used: 2-amino-5-nitropyridine
  Yield: 0.025 g (56% of theory) Mass Spectrum MH$^+$ 303(100)

c3. 2-[(2-aminoethylamino)methyl]-1,4-diaminobenzene hydrochloride
Amine Used: ethylenediamine
  Yield: 0.025 g (77% of theory) Mass Spectrum MH$^+$ 181(100)

d3. 3-[2-(2,5-diaminobenzylamino)-1-hydroxyethyl]phenol hydrochloride
Amine Used: 1-(3-hydroxyphenyl)-2-aminoethanol
  Yield: 0.025 g (65% of theory) Mass Spectrum MH$^+$ 274(100)

e3. 2-[(4-methylpyridin-2-ylamino)methyl]-1,4-diaminobenzene hydrochloride
Amine Used: 2-picolylamine
  Yield: 0.022 g (65% of theory) Mass Spectrum MH$^+$ 229(100)

f3. 2-(2,5-diaminobenzyl)-1-methyl-1,2,3,4-tetrahydroisoquinoline-6,7-diol hydrochloride
Amine Used: 1-methyl-6,7-dihydroxy-1,2,3,4-tetrahydroisoquinoline
  Yield: 0.015 g (37% of theory) Mass Spectrum MH$^+$ 300(100)

g3. 2-(2,5-diaminobenzylamino)-4-methylsulfanylbutyric acid hydrochloride
Amine Used: 2-amino-4-methylmercaptobutyric acid
  Yield: 0.015 g (32% of theory)

h3. 1-(2,5-diaminobenzyl)pyrrolidine-2-carboxylic acid hydrochloride
Amine Used: pyrrolidin-2-carboxylic acid
  Yield: 0.025 g (72% of theory) Mass Spectrum MH$^+$ 236(55)

i3. 2-phenylaminomethyl-1,4-diaminobenzene hydrochloride
Amine Used: aniline
  Yield: 0.025 g (77% of theory) Mass Spectrum MH$^+$ 214(100)

j3. 2-(4-dimethylaminophenyl)aminomethyl-1,4-diaminobenzene hydrochloride
Amine Used: 4-amino-N,N-dimethylaniline
  Yield: 0.025 g (62% of theory) Mass Spectrum MH$^+$ 257(100)

k3. 1-[3-(2,5-diaminobenzylamino)phenyl]ethanol hydrochloride
Amine Used: 3-(1-hydroxyethyl)aniline
  Yield: 0.025 g (68% of theory) Mass spectrum MH$^+$ 258(100)

l3. 2-[(3,4-dimethoxyphenylamino)methyl]-1,4-diaminobenzene hydrochloride
Amine Used: 3,4-dimethoxyaniline
  Yield: 0.025 g (65% of theory) Mass Spectrum MH$^+$ 274(100)

m3. 2-[(3-fluoro-2-methoxyphenylamino)methyl]-1,4-diaminobenzene hydrochloride
Amine Used: 3-fluoro-2-methoxyaniline
Yield: 0.021 g (57% of theory) Mass Spectrum MH$^+$ 262(100)

n3. 4-chloro-2-(2,5-diaminobenzylamino)phenol hydrochloride
Amine Used: 4-chloro-2-aminophenol
Yield: 0.025 g (67% of theory) Mass Spectrum MH$^+$ 264(100)

o3. 2-[(4-trifluoromethylphenylamino)methyl]-1,4-diaminobenzene hydrochloride
Amine Used: 4-trifluoromethylaniline
Yield: 0.025 g (64% of theory) Mass Spectrum MH$^+$ 282(100)

p3. 2-(p-tolylaminomethyl)-1,4-diaminobenzene hydrochloride
Amine Used: 4-methylaniline
Yield: 0.025 g (74% of theory) Mass Spectrum MH$^+$ 228(100)

Example 2

Synthesis of 2-(1-aminoethyl)-1,4-diaminobenzene Compounds

A. Synthesis of (4-tert.-butoxycarbonylamino-3-(1-hydroxyethyl)phenyl)carbamic acid tert.-butyl ester 3.3 g (0.01 mol) (4-tert.butoxycarbonylamino-3-bromophenyl)carbamic acid-tert.-butyl ester are dissolved in 200 ml diethyl ether under argon. Then first 20 ml of a 1.6 molar methyl lithium solution are added at −25° C. and then 16 ml of a 1.6 molar tert.-butyl lithium solution are added. After one hour 1.2 ml (0.02 mol) of acetaldehyde are added and the reaction mixture is slowly heated to 20° C. After halting the reaction the reaction mixture is hydrolyzed with water, the organic phase is extracted with dilute sodium hydroxide and then dried with magnesium sulfate. The solvent is distilled off in a rotary evaporator and the residue is purified with petroleum ether/acetic acid ethyl ester (8:2). 3.0 g (85% of theoretical) of (4-tert.-butoxycarbonylamino-3-(1-hydroxyethyl)phenyl)carbamic acid-tert.-butyl ester having a melting point of 189° C. are obtained.

B. Synthesis of (4-tert.-butoxycarbonylamino-3-(1-aminoethyl)phenyl)carbamic acid tert.-butyl ester 3.5 g of the (4-tert.-butoxycarbonylamino-3-(1-hydroxyethyl)phenyl)carbamic acid-tert.-butyl ester (0.01 mol) from step A are dissolved in 30 ml of dichloromethane. Then 1.3 g (0.013 mol) triethylamine and 2.4 g (0.01 mol) mesitylene sulfochloride are added at 4° C. The solution is first stirred for an hour at 4° C. and subsequently stirred for one hour at room temperature. The solvent is distilled off in a rotary evaporator and the residue is purified on silica gel with hexane/ethyl acetate (1:5).

Subsequently the product is dissolved in 30 ml of dimethylsulfoxide and reacted with 3.5 g (0.05 mol) sodium azide and then the reaction mixture is heated to 60° C. After halting the reaction the reaction mixture is poured into ethyl acetate/water and the organic phase is dried with magnesium sulfate. The solvent is distilled off in a rotary evaporator and the residue is purified on silica gel with ethyl acetate/hexane (1:6).

The product obtained is dissolved in ethanol and hydrogenated at 25° C. under addition of 200 mg of a palladium-activated carbon catalyst (10%) and 1.8 g (0.03 mol) acetic acid. After four hours the catalyst is removed by filtration. The solvent is distilled off in a rotary evaporator and the residue is purified on silica gel with chloroform/methanol/triethylamine (50:10:1).

1.0 g (28% theoretical) of (4-tert.-butoxycarbonylamino-3-(1-aminoethyl)phenyl)carbamic acid tert.-butyl ester with a melting point of 170° C. were obtained.

C. Synthesis of 1,4-diamino-2-(1-aminoethyl)benzene Compounds 0.033 g (0.0001 mol) (4-tert.-butoxycarbonylamino-3-(1-aminoethylphenyl)carbamic acid-tert.-butyl ester from step B and 0.00015 mol of a suitable aldehyde are dissolved in 1,2-dichloroethane. Subsequently 0.1 ml of an acetic acid solution (1M in 1,2-dichloroethane) and 0.06 g (0.0003 mol) NaBH(OAc)$_3$ are added and the reaction mixture is stirred for 5 to 15 hours. After terminating the reaction the reaction mixture is poured into 10 ml acetic acid ethyl ester, the organic phase is extracted with sodium hydrogen carbonate and then dried with magnesium sulfate. The solvent is distilled off with a rotary evaporator and the residue is purified on silica gel with petroleum ether/ethyl acetate (9:1). The product thus obtained is heated in 4 ml of ethanol at 50° C.

Subsequently 1.5 ml of a 2.9 molar ethanolic hydrochloric acid solution is added dropwise to make the hydrochloride. The precipitate is filtered off, washed twice with 1 ml of ethanol and then dried.

a. 1,4-diamino-2-(1-butylaminoethyl)benzene hydrochloride
Aldehyde Derivative Used: butyraldehyde
Yield: 0.025 g (78% of theory) Mass Spectrum MH$^+$ 208(100)

b. 1,4-diamino-2-{1-(3-methylbutylamino)ethyl}benzene hydrochloride
Aldehyde Derivative Used: 3-methylbutryaldehyde
Yield: 0.025 g (75% of theory) Mass Spectrum MH$^+$ 222(100)

c. 1,4-diamino-2-(1-benzylaminoethyl)benzene hydrochloride
Aldehyde Derivative Used: benzaldehyde
Yield: 0.025 g (71% of theory) Mass Spectrum MH$^+$ 242(100)

d. 1,4-diamino-2-{1-[(pyridin-2-ylmethyl)amino]ethyl}benzene hydrochloride
Aldehyde Derivative Used: pyridin-2-carbaldehyde
Yield: 0.025 g (64% of theory) Mass Spectrum MH$^+$ 243(20)

e. 1,4-diamino-2-{1-[(pyridin-3-ylmethyl)amino]ethyl}benzene hydrochloride
Aldehyde Derivative Used: pyridin-3-carbaldehyde
Yield: 0.025 g (64% of theory) Mass Spectrum MH$^+$ 243(50)

f. 1,4-diamino-2-{1-[(pyridin-4-ylmethyl)amino]ethyl}benzene hydrochloride
Aldehyde Derivative Used: pyridin-4-carbaldehyde
Yield: 0.025 g (64% of theory) Mass Spectrum MH$^+$ 243(100)

g. 1,4-diamino-2-{1-[(thiophen-2-ylmethyl)amino]
ethyl}benzene hydrochloride
Aldehyde Derivative Used: thiophen-2-carbaldehyde
   Yield: 0.025 g (70% of theory) Mass Spectrum MH$^+$
248(100)

h. 1,4-diamino-2-{1-[(thiophen-3-ylmethyl)amino]
ethyl}benzene hydrochloride
Aldehyde Derivative Used: thiophen-3-carbaldehyde
   Yield: 0.025 g (70% of theory) Mass Spectrum MH$^+$
248(100)

i. 1,4-diamino-2-{1-(cyclohexylmethylamino)
ethyl}benzene hydrochloride
Aldehyde Derivative Used: cyclohexanecarbaldehyde
   Yield: 0.025 g (70% of theory) Mass Spectrum MH$^+$
248(100)

j. 4-{[1-(2,5-diaminophenyl)ethylamino]
methyl}benzene hydrochloride
Aldehyde Derivative Used: 4-hydroxybenzaldehyde
   Yield: 0.025 g (68% of theory) Mass Spectrum MH$^+$
258(100)

k. 1,4-diamino-2-[1-(4-dimethylaminobenzylamino)
ethyl]benzene hydrochloride
Aldehyde Derivative Used: 4-dimethylaminobenzaldehyde
   Yield: 0.020 g (46% of theory) Mass Spectrum MH$^+$
285(100)

l. 1,4-diamino-2-(1-(4-nitrobenzylamino)ethyl]
benzene hydrochloride
Aldehyde Derivative Used: 4-nitrobenzaldehyde
   Yield: 0.025 g (63% of theory) Mass Spectrum MH$^+$
286(100)

m. 2-{[1-(2,5-diaminophenyl)ethylamino]methyl}-
4-nitrophenol hydrochloride
Aldehyde Derivative Used: 2-hydroxy-5-nitrobenzaldehyde
   Yield: 0.025 g (60% of theory) Mass Spectrum MH$^+$
303(100)

n. 1,4-diamino-2-{1-(4-pyrrolidin-1-ylbenzylamino)
ethyl}benzene hydrochloride
Aldehyde Derivative Used: 4-pyrrolidinobenzaldehyde
   Yield: 0.025 g (54% of theory) Mass Spectrum MH$^+$ 311
(100)

p. 1,4-diamino-2-{1-[(benzo[1,3]dioxol-5-ylmethyl)
amino]ethyl}benzene hydrochloride
Aldehyde Derivative Used: 3,4-methylendioxybenzaldehyde
   Yield: 0.025 g (63% of theory) Mass Spectrum MH$^+$
286(100)

q. 1,4-diamino-2-{1-(3-chlorobenzylamino)
ethyl}benzene hydrochloride
Aldehyde Derivative Used: 3-chlorobenzaldehyde
   Yield: 0.025 g (64% of theory) Mass Spectrum MH$^+$
276(100)

D. Synthesis of 1,4-diamino-2-(1-aminoethyl)
benzene Compounds
0.033 g (0.0001 mol) (4-tert-butoxycarbonylamino-3-(1-aminoethyl)phenyl)carbamic acid-tert.-butyl ester from step B are dissolved in 25 ml ethanol. Subsequently 0.00015 mol of a suitable fluoro derivative are added. After termination of the reaction the reaction mixture is poured into water, the aqueous phase is extracted with ethyl acetate and then dried with magnesium sulfate. The solvent is distilled off in a rotary evaporator and the residue is purified on silica gel with hexane/ethyl acetate (5:1). The product thus obtained is heated in 4 ml of ethanol at 50° C. Subsequently 1.5 ml of a 2.9 molar ethanolic hydrochloric acid solution were added dropwise. The precipitate was filtered off, washed twice with 1 ml of ethanol and then dried.

r. 1,4-diamino-2-[1-(2-nitrophenylamino)ethyl]
benzene hydrochloride
Fluoride Derivative Used: 1-fluoro-2-nitrobenzene
   Yield: 0.025 g (65% of theory) Mass Spectrum MH$^+$
273(100)

s. 1,4-diamino-2-[1-(4-fluoro-2-nitrophenylamino)
ethyl]benzene hydrochloride
Fluoride Derivative Used: 1,4-difluoro-3-nitrobenzene
   Yield: 0.020 g (50% of theory) Mass Spectrum MH$^+$ 291
(100)

t. 1,4-diamino-2-[1-(5-fluoro-2-nitrophenylamino)
ethyl]benzene hydrochloride
Fluoride Derivative Used: 1,5-difluoro-2-nitrobenzene
   Yield: 0.025 g (62% of theory)

u. 1,4-diamino-2-[1-(2-fluoro-6-nitrophenylamino)
ethyl]benzene hydrochloride
Fluoride Derivative Used: 1,2-difluoro-6-nitrobenzene
   Yield: 0.025 g (62% of theory) Mass Spectrum MH$^+$ 291
(100)

v. 2-[1-(2,5-diaminophenyl)ethylamino]-5-
nitrobenzoic acid hydrochloride
Fluoride Derivative Used: 2-fluoro-5-nitrobenzoic acid
   Yield: 0.025 g (64% of theory) Mass Spectrum MH$^+$
317(100)

w. 1,4-diamino-2-[1-(4-bromo-2-nitrophenylamino)
ethyl]benzene hydrochloride
Fluoride Derivative Used: 1-bromo-4-fluoro-3-nitrobenzene
   Yield: 0.01 8 g (39% of theory)

x. 1,4-diamino-2-[1-(4-amino-2-nitrophenylamino)
ethyl]benzene hydrochloride
Fluoride Derivative Used: 1-fluoro-2-nitro4-aminobenzene
   Yield: 0.01 6 g (36% of theory) Mass Spectrum MH$^+$
288(80)

Examples 3 to 70

Oxidation Hair Dye Precursor Compositions
Hair dye precursor solutions with the following compositions were prepared:

| | |
|---|---|
| 0.0125 mmol | developer substance of formula (I) according to Table I |
| 0.0125 mmol | coupler substance according to Table I |
| 0.01 g | potassium oleate (8 percent aqueous solution) |
| 0.01 g | ammonia (22 percent aqueous solution) |
| 0.01 g | ethanol |
| 0.003 g | ascorbic acid |
| to 1.0 g | water |

1 g of the above-described dye precursor solution is mixed with 1 g of a 6 percent aqueous hydrogen peroxide solution immediately prior to application. Subsequently the mixture is applied to bleached hair. After an acting time of 30 minutes at 40° C. the hair is rinsed with water, washed with a commercially obtained shampoo and dried. The resulting dyed hair colors are tabulated in Table I.

TABLE I

DYED HAIR COLORS OBTAINED WITH THE OXIDATION DYE PRECURSOR COMPOSITIONS ACCORDING TO THE INVENTION

| Example | Developer Of Formula I From Ex. 1 | 1,3-di-hydroxy-benzene coupler | 1,3-diamino-4-(2-hydroxyethoxy)-benzene sulfate coupler | 5-amino-2-methyl phenol coupler | 1-naphthol coupler |
|---|---|---|---|---|---|
| 3 | a1 | Bright light Blond | Gray-blue | Medium Purple | Gray-rose |
| 4 | b1 | Bright light Blond | Blue | Bright Purple | Bright Gray-rose |
| 5 | c1 | Bright light Blond | Gray-blue | Bright Purple | Gray-rose |
| 6 | d1 | Bright blond | Blue | Medium Purple | Bright Purple |
| 7 | e1 | Bright light Blond | Gray-blue | Bright Purple | Gray-rose |
| 8 | f1 | Bright blond | Blue | Medium Purple | Violet |
| 9 | g1 | Bright light Blond | Blue | Medium Purple | Gray-rose |
| 10 | h1 | Bright light Blond | Blue | Medium Purple | Gray-rose |
| 11 | i1 | Bright blond | Blue | Medium Purple | Violet |
| 12 | j1 | Bright blond | Blue | Bright Purple | Gray-rose |
| 13 | k1 | Bright Blond | Blue | Medium Purple | Gray-rose |
| 14 | l1 | Bright light Blond | Blue | Bright Purple | Gray-rose |
| 15 | m1 | Bright light Blond | Blue | Bright Purple | Bright Purple |
| 16 | n1 | Bright light Blond | Blue | Bright Purple | Gray-rose |
| 17 | o1 | Bright Blond | Blue | Medium Purple | Bright Gray-rose |
| 18 | p1 | Bright light Blond | Blue | Bright Purple | Gray-rose |
| 19 | q1 | Bright light Blond | Blue | Bright Purple | Gray-rose |
| 20 | r1 | Blue | Deep blue | Blue | Deep blue |
| 21 | s1 | Red-brown | Gray-blue | Gray-rose | Gray-rose |
| 22 | t1 | Bright rose | Bright Blue-gray | Bright Rose | Gray-rose |
| 23 | u1 | Bright light Blond | Bright Gray-blue | Bright Purple | Bright Gray-rose |
| 24 | v1 | Bright light Blond | Blue | Bright Purple | Gray-rose |
| 25 | w1 | Bright light Blond | Blue | Bright Purple | Gray-rose |
| 26 | x1 | Bright ash Blond | Blue | Medium Purple | Violet |
| 27 | y1 | Bright Blond | Blue | Medium Purple | Violet |
| 28 | z1 | Bright light Blond | Gray-blue | Bright Purple | Gray-rose |
| 29 | a2 | Gold blond | Gray | Medium Purple | Medium Purple |
| 30 | b2 | Bright light Blond | Blue | Bright Purple | Gray-rose |
| 31 | c2 | Bright blond | Blue | Medium Purple | Gray-rose |
| 32 | d2 | Medium purple | Blue | Medium Purple | Violet |
| 33 | e2 | Bright light Blond | Blue | Medium Purple | Medium Purple |
| 34 | f2 | Bright light Blond | Blue | Bright Purple | Gray-rose |
| 35 | g2 | Violet | Deep blue | Violet | Blue |
| 36 | h2 | Violet | Deep blue | Violet | Violet |
| 37 | i2 | Deep blue | Deep blue | Gray-rose | Gray-blue |
| 38 | j2 | Bright light Blond | Gray-blue | Medium Purple | Gray-rose |

TABLE I-continued

DYED HAIR COLORS OBTAINED WITH THE OXIDATION DYE
PRECURSOR COMPOSITIONS ACCORDING TO THE INVENTION

| Example | Developer Of Formula I From Ex. 1 | 1,3-di-hydroxy-benzene coupler | 1,3-diamino-4-(2-hydroxyethoxy)-benzene sulfate coupler | 5-amino-2-methyl phenol coupler | 1-naphthol coupler |
|---|---|---|---|---|---|
| 39 | k2 | Gray-blue | Gray-blue | Gray-blue | Gray-blue |
| 40 | l2 | Bright Blond | Blue | Medium Purple | Gray-rose |
| 41 | m2 | Bright blond | Blue | Medium Purple | Gray-rose |
| 42 | n2 | Bright blond | Blue | Medium Purple | Bright Gray-rose |
| 43 | o2 | Bright Blond | Blue | Medium Purple | Gray-rose |
| 44 | p2 | Bright Blond | Blue | Medium Purple | Gray-rose |
| 45 | q2 | Bright light Blond | Blue | Medium Purple | Bright Gray-rose |
| 46 | r2 | Bright blond | Deep blue | Purple | Violet |
| 47 | s2 | Bright light Blond | Bright Gray-blue | Bright Purple | Bright Rose |
| 48 | t2 | Bright light Blond | Blue | Medium Purple | Gray-rose |
| 49 | u2 | Bright light Blond | Gray-blue | Medium Purple | Gray-rose |
| 50 | v2 | Bright light Blond | Gray-blue | Bright Purple | Gray-rose |
| 51 | w2 | Bright Purple | Bright gray | Bright Purple | Bright Purple |
| 52 | x2 | Bright ash Blond | Gray-blue | Not available | Gray-rose |
| 53 | y2 | Bright light Blond | Gray-blue | Bright Purple | Bright Gray-rose |
| 54 | z2 | Bright light Blond | Gray-blue | Bright Purple | Gray-rose |
| 55 | a3 | Bright light Blond | Blue | Bright Purple | Bright Purple |
| 56 | b3 | Bright light Blond | Gray-blue | Bright Purple | Gray-rose |
| 57 | c3 | Bright light Blond | Gray-blue | Purple | Gray-rose |
| 58 | d3 | Bright light Blond | Gray-blue | Medium Purple | Gray-rose |
| 59 | e3 | Bright Blond | Deep blue | Medium Purple | Violet |
| 60 | f3 | Bright light Blond | Bright Gray-blue | Bright Purple | Gray-rose |
| 61 | g3 | Bright light Blond | Bright Gray-blue | Bright Rose | Bright Gray-rose |
| 62 | h3 | Bright light Blond | Gray-rose | Bright Purple | Bright Gray-rose |
| 63 | i3 | Bright Blond | Deep blue | Medium Purple | Violet |
| 64 | j3 | Bright ash Blond | Gray-blue | Purple | Gray-rose |
| 65 | k3 | Bright ash Blond | Blue Purple | Medium | Violet |
| 66 | l3 | Gray | Blue | Violet | Gray-rose |
| 67 | m3 | Bright Blond | Blue | Medium Purple | Violet |
| 68 | n3 | Bright Blond | Gray-blue | Gray Purple | Gray-rose |
| 69 | o3 | Bright Blond | Blue | Medium Purple | Bright Violet |
| 70 | p3 | Bright Blond | Blue | Medium Purple | Violet |

Examples 71 to 80

Oxidation Hair Dye Precursor Compositions

Hair dye precursor solutions with the following compositions were prepared:

| | |
|---|---|
| X g | developer substances E1 to E1" of formula (I) according to Table II |
| U g | developer substances E2 to E9 according to Table II |
| Y g | coupler substances K11 to K36 according to Table IV |
| Z g | direct-dyeing dye compounds D1 to D3 according to Table III |
| 10.000 g | potassium oleate (8 percent aqueous solution) |
| 10.000 g | ammonia (22 percent aqueous solution) |
| 10.000 g | ethanol |
| 0.300 g | ascorbic acid |
| to 100.000 g | water |

30 g of the above-described dye precursor solution are mixed with 30 g of a 6 percent aqueous hydrogen peroxide solution immediately prior to application. Subsequently the mixture is applied to hair. After an acting time of 30 minutes at 40° C. the hair is rinsed with water, washed with a commercially obtained shampoo and dried. The resulting dyed hair colors are given in Table V.

Examples 81 to 86

Oxidation Hair Dye Precursor Compositions

Hair dye precursor creams with the following compositions were prepared:

| | |
|---|---|
| X g | developer substances E1 to E1" of formula (I) according to Table II |
| Y g | coupler substances K11 to K36 according to Table IV |
| Z g | direct-dyeing dye compound D2 according to Table III |
| 15.0 g | cetyl alcohol |
| 0.3 g | ascorbic acid |
| 3.5 g | sodium lauryl alcohol diglycol ether sulfate, 28% aqueous solution |
| 3.0 g | ammonia, 22% aqueous solution |
| 0.3 g | sodium sulfite, water-free |
| to 100 g | water |

30 g of the above-described dye precursor cream are mixed with 30 g of a 6 percent aqueous hydrogen peroxide solution immediately prior to application. Subsequently the mixture is applied to hair. After an acting time of 30 minutes the hair is rinsed with water, washed with a commercially obtained shampoo and dried. The resulting dyed hair colors are given in Tables VI.

Examples 87 to 110

Oxidation Hair Dye Precursor Compositions

Hair dye precursor solutions with the following compositions were prepared:

| | |
|---|---|
| 0.0125 mmol | developer substance of formula (I) according to Table VII |
| 0.0125 mmol | coupler substance according to Table VII |
| 0.01 g | potassium oleate (8 percent aqueous solution) |
| 0.01 g | ammonia (22 percent aqueous solution) |
| 0.01 g | ethanol |
| 0.003 g | ascorbic acid |
| to 1.0 g | water |

1 g of the above-described dye precursor solution is mixed with 1 g of a 6 percent aqueous hydrogen peroxide solution immediately prior to application. Subsequently the mixture is applied to bleached hair. After an acting time of 30 minutes at 40° C. the hair is rinsed with water, washed with a commercially obtained shampoo and dried. The resulting dyed hair colors are tabulated in Table VII.

TABLE II

DEVELOPER SUBSTANCES

| | |
|---|---|
| E1 | 2-phenylaminomethyl-1,4-diaminobenzene hydrochloride (according to example 1, i3) |
| E1' | 2-[(4-methylpyridin-2-ylamino)methyl]-1,4-diaminobenzene hydrochloride (according to example 1,e3) |
| E1" | 2-[(2,5-diaminobenzyl)-(2-hydroxyethyl)amino]ethanol hydrochloride (according to example 1,l2) |
| E2 | 1,4-diaminobenzene |
| E3 | 2,5-diaminophenylethanol sulfate |
| E4 | 3-methyl-4-aminophenol |
| E5 | 4-amino-2-aminomethyphenol dihydrochloride |
| E6 | 4-aminophenol |
| E7 | N,N-bis(2'-hydroxyethyl)-p-phenylenediamine sulfate |
| E8 | 4,5-diamino-1-(2-hydroxyethyl)pyrazole sulfate |
| E9 | 2,5-diaminotoluene sulfate |

TABLE III

DIRECT-DYEING DYE COMPOUNDS

| | |
|---|---|
| D1 | 2,6-diamino-3-((pyridin-3-yl)azo)pyridine |
| D2 | 6-chloro-2-ethylamino-4-nitrophenol |
| D3 | 2-amino-6-chloro-4-nitrophenol |

TABLE IV

DEVELOPER SUBSTANCES

| | |
|---|---|
| K11 | 1,3-diaminobenzene |
| K12 | 2-amino-4-(2'-hydroxyethyl)aminoanisole sulfate |
| K13 | 1,3-diamino-4-(2'-hydroxyethoxy)benzene sulfate |
| K14 | 2,4-diamino-5-fluorotoluene sulfate |
| K15 | 3-amino-2-methylamino-6-methoxypyridine |
| K16 | 3,5-diamino-2,6-dimethoxypyridine dihydrochloride |
| K17 | 2,4-diamino-5-ethoxytoluene sulfate |
| K18 | N-(3-dimethylamino)phenylurea |
| K19 | 1,3-bis-(2,4-diaminophenoxy)propane tetrahydrochloride |
| K21 | 3-aminophenol |
| K22 | 5-amino-2-methylphenol |
| K23 | 3-amino-2-chloro-6-methylphenol |
| K24 | 5-amino-4-fluoro-2-methylphenol sulfate |
| K25 | 1-naphthol |
| K26 | 1-acetoxy-2-methylnaphthalene |
| K31 | 1,3-dihydroxybenzene |
| K32 | 2-methyl-1,3-dihydroxybenzene |
| K33 | 1-chloro-2,4-dihydroxybenzene |
| K34 | 4-(2'-hydroxyethyl)amino-1,2-methylenedioxybenzene Hydrochloride |
| K35 | 3,4-methylenedioxyphenol |
| K36 | 2-amino-5-methylphenol |

TABLE V

HAIR DYE PRECURSOR COMPOSITIONS AND DYED HAIR COLORS OBTAINED THEREWITH

| Exemplary Dyestuff* | 71 | 72 | 73 | 74 |
|---|---|---|---|---|
| E1 | 0.35 | | | 0.30 |
| E1' | | 0.30 | | |
| E1" | | | 0.30 | |
| E4 | 0.30 | | | |
| E5 | | 0.30 | | |
| E6 | | | 0.30 | |
| E8 | | | | 0.30 |
| K31 | 0.18 | | | 0.20 |
| K32 | | 0.22 | | |
| K33 | | | 0.20 | |
| K25 | 0.30 | 0.30 | | 0.30 |
| K26 | | | 0.35 | |
| Dyed Hair Color | Red-brown | Red-brown | Red-brown | Red-brown |

| Exemplary Dyestuff* | 75 | 76 | 77 | 78 | 79 | 80 |
|---|---|---|---|---|---|---|
| E1 | 0.50 | | | 0.16 | | |
| E1' | | 0.40 | | | 0.15 | |
| E1" | | | 0.40 | | | 0.15 |
| E2 | | | | 0.15 | | |
| E3 | | | | | 0.15 | |
| E9 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | 0.10 | 0.10 | | |
| K33 | | | 0.20 | | | |
| K21 | 0.05 | | | | | |
| K22 | | 0.05 | | | | |
| K23 | | | 0.05 | 0.10 | 0.10 | 0.10 |
| Dyed Hair Color | Blond | Blond | Blond | Blond | Blond | Blond |

*amounts of dyestuffs are in grams

TABLE VI

HAIR DYE PRECURSOR COMPOSITIONS AND DYED HAIR COLORS OBTAINED THEREWITH

| Exemplary Dyestuff* | 81 | 82 | 83 | 84 | 85 | 86 |
|---|---|---|---|---|---|---|
| E1 | 2.50 | | | 0.90 | | |
| E1' | | 2.50 | | | 0.90 | |
| E1" | | | 2.50 | | | 0.90 |
| K12 | | | | 0.10 | 0.10 | 0.10 |
| K13 | 1.10 | 1.10 | 1.10 | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Dyed Hair Colors | Black | Black | Black | Brown | Brown | Brown |

*amounts of dyestuffs are in grams

TABLE VII

DYED HAIR COLORS OBTAINED WITH THE OXIDATION DYE PRECURSOR COMPOSITIONS ACCORDING TO THE INVENTION

| Example | Developer Of Formula I From Ex. 1 | 1,3-di-hydroxy-benzene coupler | 1,3-diamino-4-(2-hydroxyethoxy)-benzene sulfate coupler | 5-amino-2-methyl phenol coupler | 1-naphthol coupler |
|---|---|---|---|---|---|
| 87 | a | Bright light Blond | Gray-blue | Purple | Gray-rose |
| 88 | b | Bright light Blond | Blue | Bright Purple | Gray-rose |
| 89 | c | Bright light Blond | Gray-blue | Purple | Gray-rose |
| 90 | d | Bright blond | Blue | Medium Purple | Violet |
| 91 | e | Bright light Blond | Gray-blue | Bright Purple | Gray-rose |
| 92 | f | Bright blond | Blue | Medium Purple | Gray-Violet |
| 93 | g | Bright light Blond | Gray-blue | Bright Purple | Gray-rose |
| 94 | h | Bright Blond | Gray-blue | Purple | Violet |
| 95 | i | Bright blond | Gray-blue | Bright Purple | Bright Violet |
| 96 | j | Bright blond | Blue | Medium Purple | Gray-rose |
| 97 | k | Bright light Blond | Blue | Bright Purple | Gray-rose |
| 98 | l | Bright Blond | Blue | Purple | Violet |
| 99 | m | Yellow | Brown | Red-brown | Red-brown |
| 100 | n | Bright light Blond | Gray | Bright Purple | Bright Violet |
| 101 | o | Bright Blond | Blue | Medium Purple | Bright Gray-rose |
| 102 | p | Bright light Blond | Gray-blue | Bright Purple | Bright Violet |

TABLE VII-continued

DYED HAIR COLORS OBTAINED WITH THE OXIDATION DYE
PRECURSOR COMPOSITIONS ACCORDING TO THE INVENTION

| Example | Developer Of Formula I From Ex. 1 | 1,3-di-hydroxy- benzene coupler | 1,3-diamino-4-(2- hydroxyethoxy)- benzene sulfate coupler | 5-amino- 2-methyl phenol coupler | 1-naphthol coupler |
|---|---|---|---|---|---|
| 103 | q | Bright light Blond | Gray-blue | Bright Purple | Bright Violet |
| 104 | r | Bright blond | Gray | Red wine | Gray-black |
| 105 | s | Green | Blue-black | Red wine | Gray |
| 106 | t | Bright blond | Gray-blue | Bright Purple | Gray |
| 107 | u | Bright light Blond | Gray-blue | Medium Purple | Bright Gray-rose |
| 108 | v | Bright light Blond | Gray-blue | Red-brown | Gray |
| 109 | w | Bright light Blond | Gray-blue | Medium Purple | Gray |
| 110 | x | Bright Purple | Bluish red | Medium Purple | Violet |

Unless otherwise indicated all percentages are percentages by weight.

The disclosure in German Patent Application 199 61 272.2 of Dec. 18, 1999 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in substituted 2-aminoalkyl-1,4-diaminobenzene compounds and dye compositions containing same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A substituted 2-aminoalkyl-1,4-diaminobenzene compound of the formula (I):

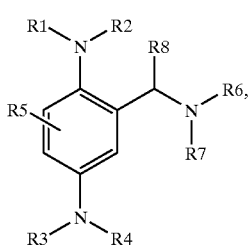

(I)

wherein R1, R2, R3 and R4, independently of each other, are each hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_2$-)alkyl group, or R1 and R2 together with N form a four member to eight member aliphatic ring; and wherein at least two of said R1, R2, R3 and R4 represent hydrogen and wherein R3 and R4 are not both simultaneously a $C_1$- to $C_6$-alkyl group;

R5 represents hydrogen, a halogen atom, a $C_1$- to $C_4$-alkyl group, a $C_1$- to $C_4$-hydroxyalkyl group or a $C_1$- to $C_4$-alkoxy group;

R6 and R7, independently of each other, each represent hydrogen, a $C_1$- to $C_2$-alkoxy group, a $C_1$- to $C_6$-alkyl group, a $C_1$- to $C_6$-alkenyl group, a $C_1$- to $C_4$-hydroxyalkyl group, a $C_3$- to $C_4$-dihydroxyalkyl group, a $C_1$- to $C_4$-aminoalkyl group, a $C_1$- to $C_4$-dimethylaminoalkyl group, a $C_1$- to $C_4$-acetylamino-alkyl group, a $C_1$- to $C_4$-methoxyalkyl group, a $C_1$- to $C_4$-ethoxyalkyl group, a $C_1$- to $C_4$-cyanoalkyl group, a $C_1$- to $C_4$-carboxyalkyl group, a $C_1$- to $C_4$-aminocarbonylalkyl group, a pyridylmethyl group, a furfuryl group, a hydrogenated furfuryl group, a substituted pyridyl group, a group of the formula II:

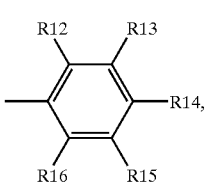

(II)

a group of the formula III:

(III)

a group of the formula IV:

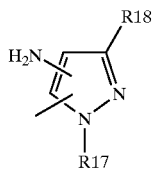

(IV)

wherein at least one of R6 and R7 is not hydrogen or R6 and R7 together with N form one of the following rings:

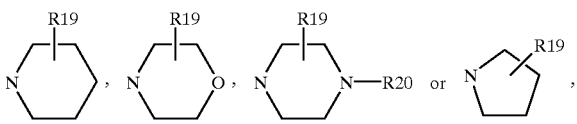

R8 represents hydrogen or a $C_1$- to $C_6$-alkyl group;
R9 represents hydrogen, a carboxy group or an aminocarbonyl group;
R10 and R11, independently of each other, each represent hydrogen, a hydroxy group, an aminocarbonyl group, a methylthiomethyl group, a substituted phenyl group having a phenyl group substituent or a hydroxy group substitutent or a group of the formula:

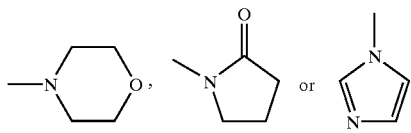

wherein R12, R13, R14, R15 and R16 are each, independently of each other, hydrogen, a halogen atom, a cyano group, a hydroxy group, a $C_1$- to $C_4$-alkoxy group, a $C_1$- to $C_4$-hydroxyalkoxy group, a $C_1$- to $C_6$-alkyl group, a $C_1$- to $C_4$-alkylthioether group, a mercapto group, a nitro group, an amino group, an alkylamino group, an alkylamino group, hydroxyalkylamino group, a dialkylamino group, a di(hydroxyalkyl)amino group, a (dihydroxyalkyl)amino group, a (hydroxyalkyl)-alkylamino group, a trifluoromethane group, a —C(O)H group, a —C(O)CH$_3$ group, a —C(O)CF$_3$ group, a —Si(CH$_3$)$_3$ group, a $C_1$- to $C_4$-hydroxyalkyl group, a $C_3$- to $C_4$-dihydoxyalkyl group, or two of the groups R12 to R16 next to each other form an —O—CH$_2$—O— bridge;
R17 represents a $C_1$- to $C_4$-alkyl group or a $C_1$- to $C_4$-hydroxyalkyl group;
R18 represents hydrogen or a $C_1$- to $C_6$-alkyl group;
R19 represents one or more hydrogen, hydroxy, carboxy, aminocarbonyl or hydroxymethyl group or groups; and
R20 represents hydrogen or a $C_1$- to $C_6$-alkyl group, with the proviso that R1, R2 and R8 are not each hydrogen when (i) R5 is in the 5-position of the aromatic ring and R5 is hydrogen, a $C_1$- to $C_4$-alkyl group or a halogen atom, and when (ii) R6 and R7, independently of each other, are a $C_1$- to $C_4$-alkyl group or a phenyl group; or or a physiologically compatible, water-soluble salt thereof.

2. The substituted 2-aminoalkyl-1,4-diaminobenzene compound as defined in claim 1, wherein said R5, said R6, said R7 and said R8 are each said hydrogen.

3. The substituted 2-aminoalkyl-1,4-diaminobenzene compound as defined in claim 1, wherein said R1, said R2, said R3 and said R4 are each said hydrogen.

4. The substituted 2-aminoalkyl-1,4-diaminobenzene compound as defined in claim 1, wherein said R8 is said hydrogen; said R6 and R7 are, independently of each other each selected from the group consisting of said hydrogen, said $C_1$- to $C_4$-alkyl group, said $C_1$- to $C_4$-hydroxyalkyl group, said $C_3$- to $C_4$-dihydroxyalkyl group, said groups of formula (III) and said groups of formula (IV) or said R6 and R7 taken together an aliphatic ring of the following formula:

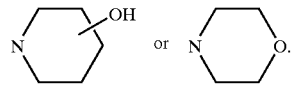

5. A substituted 2-aminoalkyl-1,4-diaminobenzene compound selected from the group consisting of 2-(2,3-dihydroxypropyl)-aminomethyl-1,4-diamino-benzene; 2-[(2-aminoethylamino)methyl]-1,4-diamino-benzene; 2-[(2-hydroxy-ethylamino)methyl]-1,4-diaminobenzene; 2-[(2,5-diaminobenzyl)methylamino]-ethanol; 2-(2,5-diaminobenzylamino)-propan-1-ol; 2-[(2,5-diaminobenzyl)-(2-hydroxyethyl)amino]ethanol; [1-(2,5-diaminobenzyl)-pyrrolidin-2-yl]methanol; 1-(2,5-diaminobenzyl)-pyrrolidin-2-carboxamide; 2-[(4-methylpyridin-2-yl-amino)-methyl]-1,4-diaminobenzene; 2-((2-aminophenyl-amino)methyl)-1,4-diamino-benzene; 2-((2-chlorophenylamino)methyl)-1,4-diaminobenzene; 2-((2-dimethylaminophenylamino)methyl)-1,4-diaminobenzene; 2-((2-fluorophenylamino)methyl)-1,4-diaminobenzene; 2-((2-hydroxyethylamino-phenylamino)methyl)-1,4-diaminobenzene; 2-((2-N,N-bis-(hydroxyethyl) aminophenylamino)methyl)-1,4-diaminobenzene; 2-((2-pyrrolidinphenylamino)methyl)-1,4-diaminobenzene; 2-((3-aminophenylamino)methyl)-1,4-diaminobenzene; 2-((3-chlorophenylamino)methyl)-1,4-diaminobenzene; 2-((3-dimethylamino-phenylamino)methyl)-1,4-diaminobenzene; 2-((3-fluorophenylamino)methyl)-1,4-diaminobenzene; 2-((3-hydroxyethylaminophenylamino)methyl)-1,4-diamino-benzene; 2-((3-N,N-bis-(hydroxyethyl) aminophenylamino)methyl)-1,4-diamino-benzene; 2-((3-pyrrolidin-phenylamino)methyl)-1,4-diaminobenzene; 2-((4-amino-phenylamino)methyl)-1,4-diaminobenzene; 2-((4-chlorophenylamino)methyl)-1,4-diaminobenzene; 2-((4-dimethylaminophenylamino)methyl)-1,4-diamino-benzene; 2-((4-fluorophenylamino)methyl)-1,4-diaminobenzene; 2-((4-hydroxyethylaminophenylamino) methyl)-1,4-diaminobenzene; 2-((4-N,N-bis-(hydroxyethyl) aminophenylamino)methyl)-1,4-diaminobenzene; 2-((4-pyrrolidinphenylamino)methyl)-1,4-diaminobenzene; 2-((2-(2-hydroxy)-ethoxy-4-aminophenylamino)methyl)-1,4-diaminobenzene; 2-((2-amino-4-aminophenylamino) methyl)-1,4-diaminobenzene; 2-((2-chloro-4-aminophenylamino)methyl)-1,4-diamino-benzene; 2-((2-hydroxy-4-aminophenylamino)methyl)-1,4-diaminobenzene; 2-((2-hydroxyethylamino-4-aminophenylamino)methyl)-1,4-diaminobenzene; 2-((2-methyl-4-aminophenylamino)methyl)-1,4-diaminobenzene; 2-((3-(2-hydroxy)-ethoxy-4-aminophenylamino)methyl)-1,4-diaminobenzene; 2-((3-amino-4-aminophenylamino) methyl)-1,4-diaminobenzene; 2-((3-chloro-4-aminophenylamino)methyl)-1,4-diaminobenzene; 2-((3-hydroxy-4-amino-phenylamino)methyl)-1,4-diaminobenzene; 2-((3-hydroxyethylamino-4-aminophenylamino)methyl)-1,4-diaminobenzene; 2-((3-methyl-4-aminophenylamino)-methyl)-1,4-diaminobenzene; 2-((2-(2- hydroxy)ethoxyphenylamino)methyl)-1,4-diaminobenzene; 2-((2-hydroxyphenylamino)methyl)-1,4-diaminobenzene; 2-((3-(2-hydroxy)ethoxyphenylamino)methyl)-1,4-diaminobenzene; 2-((3-hydroxyphenylamino)-methyl)-1,4-diaminobenzene; 2-((4-(2-hydroxy)-ethoxy-phenylamino) methyl)-1,4-diaminobenzene; 2-((4-hydroxyphenylamino) methyl)-1,4-diaminobenzene; 2-(phenylamino)methyl-1,4-diaminobenzene; 2-[5-amino-4-(2,5-diaminophenylamino)-pyrazol-1-yl]ethanol; $N^2$-(5-amino-1-methyl-1H-pyrazol-4-yl)-1,2,4-triaminobenzene; $N^2$-(5-amino-1-isopropyl-1H-pyrazol-4-yl)-1,2,4-triaminobenzene and $N^2$-(5-amino-1,3-dimethyl-1H-pyrazol-4-yl)-1,2,4-triaminobenzene.

* * * * *